Figures 1A, 1B:

United States Patent [19]

Brown et al.

[11] Patent Number: 5,262,177
[45] Date of Patent: Nov. 16, 1993

[54] RECOMBINANT VIRUSES ENCODING THE HUMAN MELANOMA-ASSOCIATED ANTIGEN

[75] Inventors: Joseph P. Brown, Seattle; Charles D. Estin, Bainbridge Island; Gregory D. Plowman; Timothy M. Rose, both of Seattle; Karl E. Hellstrom; Ingegerd Hellstrom, both of Seattle; Anthony F. Purchio, Seattle; Shiu-Lok Hu, Redmond; Sridhar Pennathur, Seattle, all of Wash.

[73] Assignee: Oncogen, Seattle, Wash.

[21] Appl. No.: 7,230

[22] Filed: Jan. 27, 1987

Related U.S. Application Data

[63] Continuation-in-part of Ser. No. 827,313, Feb. 7, 1986, abandoned.

[51] Int. Cl.$^5$ .................. A61K 39/12; C12P 21/02; C12P 19/34; C12N 15/00; C12N 7/00; C12N 5/00; C12N 1/21; C12N 1/16
[52] U.S. Cl. ..................... 424/89; 435/69.3; 435/172.3; 435/235.1; 435/320.1; 435/252.3; 435/252.33; 435/240.2; 536/23.5; 530/350; 835/9; 835/32; 835/41; 835/57; 835/65; 835/70; 835/73
[58] Field of Search ............ 435/68, 70, 172.1, 172.3, 435/235, 236, 320, 69.3, 91, 235.1, 320.1, 252.33, 255, 256, 240.2; 424/89; 536/27; 530/350; 835/9, 32, 41, 57, 65, 70, 73

[56] References Cited

U.S. PATENT DOCUMENTS 4,603,112 7/1986 Paoletti et al. .................. 435/172.1
4,719,177 12/1988 Baltimore et al. .................. 435/91

OTHER PUBLICATIONS

Brown et al., J. of Immunology, vol. 127, pp. 538–546 (1981).
Additional pages of Maniaks et al., Moleculer Cloning: A Laboratory Manual, pp. 224–228, 270–274, 350–352.
Lehninger Biochemistry 2nd Edition Worth Publishers Inc., New York, NY (1975) pp. 125–152.
Korman et al., Proc. Natl. Acad. Sciences 00179 pp. 1844–1848 (1982).
Okayama et al., Mol. Cell. Bio. vol. 2, pp. 161–170 (1982).
Helfman, D. M. et al., Proc. Natl. Acad. Sci. USA vol. 80 pp. 31–35 (1983).
Suggs et al. Proc. Nat'l. Acad Sci. USA vol. 78, pp. 6613–6617 (1981).
Maniatis et al., Molecular Cloning, A Laboratory Manual, Cold Spray Harbor Laboratory, CSH, NY (1982) pp. 404–435.
Berkner, K. L. et al., Nucl. Acids. Res. vol. 12 pp. 1925–1941 (1984).
Brown, J. P., Nature vol. 296 pp. 171–173 (1982).
Brown et al., 1980, J. Biol. Chem. 255:4980–4983 (Brown III).
Dippold et al., 1980, Proc. Natl. Acad. Sci. U.S.A. 77:6114–6118.
Woodbury et al., 1980, Proc. Natl. Acad. Sci. U.S.A., 77(4):2183–2187 (Woodbury I).
Brown et al., 1981, J. Immunol. 127:539–547 (Brown II).
Woodbury et al., 1981, Int. J. Cancer 27:145–149 (Woodbury II).
Brown et al., 1981, Proc. Natl. Acad. Sci. U.S.A. 78(1):539–543 (Brown IV).
(List continued on next page.)

Primary Examiner—Joan Ellis
Attorney, Agent, or Firm—Pennie & Edmonds

[57] ABSTRACT

Peptides or proteins related to a melanoma associated antigen are described. These are produced in large quantities via recombinant DNA techniques and/or by chemical synthetic methods. The peptides or proteins can be used as immunogens in vaccine formulations which can induce an immune response that selectively destroys melanoma cells in a vaccinated individual. Where the peptides or proteins are expressed by a recombinant virus, inactivated or live virus vaccine formulations may be prepared.

34 Claims, 12 Drawing Sheets

OTHER PUBLICATIONS

Garrigues et al., 1982, Int. J. Cancer 29:511–515.
Plowman et al., 1983, Nature 303:70–72.
Larson et al., 1983, J. Clin. Invest. 72:2101–2114.
Khosravi et al., 1985, Int. J. Cancer 35:73–80.
Shiku et al., 1876, J. Exptal. Med. 144:873–881.
Bystryn, 1978, J. Immunol. 120:96–101.
Yang et al., 1984, Proc. Natl. Acad. Sci. U.S.A. 81:2752–2756.
Metz–Boutique et al., 1984, Eur. J. Biochem. 145:657–679.
Hellstrom et al., 1968, Nature 220:1352–1354 (Hellstrom I).
Hellstrom et al., 1970, Int. J. Cancer 6:346–351 (Hellstrom II).
Hoover et al., 1985, Cancer 55:1236–1243.
Hopp & Woods, 1981, Proc. Natl. Acad. Sci. U.S.A. 78:3824–3828.
Young & Davis, 1983, Proc. Natl. Acad. Sci. U.S.A. 80:1194–1195.
Cochran et al., Eucaryotic Transient Expression System Dependent on Transcription Factors and Regulatory DNA Sequences of Vaccinia Virus, 1985, Proc. Natl. Acad. Sci. U.S.A. 82:19–23.
Haj–Amad and Graham, 1986, Development of a Helper–Independent Human Adenovirus Vector and Its Use in the Transfer of the Herpes Simplex Virus Thymidine Kinase Gene, J. Virol. 57:267–276.
Mansour et al., An Adenovirus Vector System Used to Express Polyoma Virus Tumor Antigens, 1985, Proc. Natl. Acad. Sci. U.S.A. 82:1359–1363.
Subramani and Southern, 1983, Analysis of Gene Expression Using Simian Virus 40 Vectors, Anal. Biochem. 135:1–15.
Kaufman and Sharp, 1982, Amplification and Expression of Sequences Cotransfected With a Modular Dihydrofolate Reductase Complementary DNA, Gene, J. Mol., Biol. 159:601–621.
Kuroda et al., Expression of the Influenza Virus Haemagglutin in Insect Cells by a Baculovirus Vector, 1986, EMBO J. 5:1359–1365.
Maeda et al., Production of Human a–Interferon in Silkworm Using a Baculovirus Vector, 1985, Nature (London), 315:592–594.
Kramer et al., HTLV–III gag protein Is Processed In Yeast Cells By The Virus Pol–Polymerase, 1986, Science 231:1580–1584.
Valenzuela et al., Synthesis and Assembly of Hepatitis B Virus Surface Antigen Particles in Yeast, 1982, Nature (London) 298:347.
Yanisch–Perron et al., 1985, Improved M13 Phage Cloning Vectors and Host Strains: Nucleotide Sequences of the M13mp18 and pUC19 Vectors, Gene 33:103–119.
Young and Davis, Efficient Isolation of Genes Using Antibody Probes, 1983, Proc. Natl. Acad. Sci. U.S.A. 80:1194–1198.
Dunn and Studier, Complete Nucleotide Sequence of Bacteriophage T7 DNA and the Locations of T7 Genetic Elements, 1983, J. Mol. Biol. 166:477–536.
Palmiter et al., 1983, Metallothionein–Human GH Fusion Genes Stimulate Growth of Mice, Science 222:809–814.
Taub and Thompson, 1982, an Improved Method for Preparing Large Arrays of Bacterial Colonies Containing Plasmids for Hybridization: In Situ Purification and Stable Binding of DNA on Paper Filters, Anal. Biochem. 126:222–230.
Backman and Boyer, 1983, Tetracycline Resistance Determined by pBR322 Is Mediated By Onbe Polypeptide, Gene 26:197–203.

FIG. 3A

```
TAC TAC GTG GTG GCC GTG GTG AGA CGG GAC AGC TCC CAC GCC TTC ACC TTG GAT GAG CTT CGG GGC AAG CGC TCC TGC CAC GCC GGT TTC    1440
Tyr Tyr Val Val Ala Val Val Arg Arg Asp Ser Ser His Ala Phe Thr Leu Asp Glu Leu Arg Gly Lys Arg Ser Cys His Ala Gly Phe     480

GGC AGC CCT GCA GGC GTC GAT GTC CCC GTG GGT GCC CTT ATT CAG AGA GGC TTC ATC CGG CCC AAG GAC TGT GAC CTC ACA GCA GTG         1530
Gly Ser Pro Ala Gly Val Asp Val Pro Val Gly Ala Leu Ile Gln Arg Gly Phe Ile Arg Pro Lys Asp Cys Asp Leu Thr Ala Val        510

AGC GAG TTC TTC AAT GCC AGC TGC GTG CCC GTG TGC GCA AAG AAC TAC CCC AAG AAC TAC TCC CCG CTC TGC GTG GAG CAG CAG GTT         1620
Ser Glu Phe Phe Asn Ala Ser Cys Val Pro Val Cys Ala Lys Asn Tyr Pro Lys Asn Tyr Ser Pro Leu Cys Val Glu Gln Gln Val        540

GGC CGC AAC AAG TGT GTG GGC AAC AGC CAG GAG CGG TAC TAT TAC GGC TAC CGC GGC GCC TTC AGG TGC CTG GTG GAG AAT GCG GAC GGT     1710
Gly Arg Asn Lys Cys Val Gly Asn Ser Gln Glu Arg Tyr Tyr Tyr Gly Tyr Arg Gly Ala Phe Arg Cys Leu Val Glu Asn Ala Gly Asp    570

GCC TTC GTC AGG ACA ACC ACC GTC TTT GAC AAC ACA AAC AAC GGC CAC TCC GAG CTC CTA GAG TCA GAG GAC TAT GAA                     1800
Ala Phe Val Arg Thr Thr Thr Val Phe Asp Asn Thr Asn Asn Gly His Ser Glu Leu Leu Glu Ser Glu Asp Tyr Glu                    600

CTG CTG TGC CCC AAC GGG GCC CGA GCC TCC CAG GCG TTT GCA GCC TGT AAC AAC CTG CTG GGC CAC ATA CCA CCC CAC GCC GTG ATG         1890
Leu Leu Cys Pro Asn Gly Ala Arg Ala Ser Gln Ala Phe Ala Ala Cys Asn Asn Leu Leu Gly His Ile Pro Pro His Ala Val Met        630

CCC ACC AAC ATC TTC ACC GTG TAT GGC GAG GAC GAC CAC GCC CAG GAC GAC CAC AAT AAG GAG AAA AAC ACC GGG ATG TTC AAA ATG         1980
Pro Asp Thr Asn Ile Phe Thr Val Tyr Gly Glu Asp Ala Gln Asp Asp His Asn Lys Glu Lys Asn Gly Met Phe Lys Met                660

TTC GAC TCC TCA AAC TAT CAT GGC CAA GAC CTG CTG TTC AAG GAT TCG ACC GTC CAG CAG TGC CGG GGC GCG CCC GGG GCG CGC             2070
Phe Asp Ser Ser Asn Tyr His Gly Gln Asp Leu Leu Phe Lys Asp Ser Thr Val Gln Gln Cys Arg Gly Ala Pro Gly Ala Arg            690

GGC TGG TGT CTG GGG GAC GAC TAC GTG GCG CCA CTG GAA GGG GCT CTG CCG CCG GCC CCG CCG CGG CCC GGG GCG CCC                     2160
Gly Trp Cys Leu Gly Asp Tyr Val Ala Pro Leu Glu Gly Ala Leu Pro Pro Ala Pro Pro Arg Pro Gly Ala Pro                        720

CTG CTC CCG CTG CTG CCG GCC CTC CGC GCC CGC CTC TGA GCC                                                                      2250
Leu Leu Pro Leu Leu Pro Ala Leu Ala Ala Arg Leu Pro Pro Ala Leu ***                                                         738

GCC CGG GGA GTT TCC GCG GCG GCT CGC GCT GCG GAA TCC AGA AGG AAG CTC GCG A..                                                  2308

...............................................(1280 bp)..............................

GAC GAT TGC GTT TTG TCA AAA GGG AGT TTT GTG CGG TGA GAA GTG TGT TTC GTG GCT AAC TCT GGG CTA GCG TGC CGT GGC CAT             3678

TGA AGG TGT GGG CTG CGT GGG TGC AGT GTA AGT GAC GCT GGA TTG TCA GGT GGA AGG GGG CCC GCC CTG TGT CAG GCC AGC                 3768

ATG TTG GGT TTC TAA AAT AAA GCC AAA CAA GCC ACA GCC CGA GGC TTG GAC CCT GAT AAA AAA AAA                                     3840
```

RECOMBINANT VIRUSES ENCODING THE HUMAN MELANOMA-ASSOCIATED ANTIGEN

The present application is a continuation in part of copending application Ser. No. 827,313 filed Feb. 7, 1986, now abandoned, which is hereby incorporated by reference in its entirety.

TABLE OF CONTENTS

1. Field of the Invention
2. Background of the Invention
   2.1. Tumor Associated Antigens
   2.2. Melanoma Associated p97 Antigen
   2.3. Cancer Vaccines
   2.4. Recombinant DNA Techniques and Vaccinia Virus
3. Summary of the Invention
4. Brief Description of the Figures
5. Detailed description of the Invention
   5.1. Sequence Analysis of the Melanoma Associated p97 Antigen
      5.1.1. Identification and Characterization of the Melanoma Associated p97 Antigen
      5.1.2. Identification, Cloning and Sequencing of DNA Coding for the Melanoma Associated p97 Antigen
   5.2. Synthesis of Antigenic Fragments of the Melanoma Associated p97 Antigen and Evaluation of Immunogenicity
   5.3. Production of p97 Related Peptides by Expression Vector-Host Systems
      5.3.1. Identification of Recombinant Expression Vectors Capable of Replicating and Directing the Expression of the p97 DNA Sequences
      5.3.2. Purification of the p97 Related Peptides from Expression Vector-Host Systems
   5.4. Immunological Characterization of p97 Related Peptides
   5.5. Vaccine Formulation
      5.5.1. Viral Vaccine Formulations
      5.5.2. Subunit Vaccine Formulations
6. Example: Melanoma Associated p97 Antigen
   6.1. Purification of p67 mRNA
   6.2. Preparation and Construction of cDNA Clones
      6.2.1. Construction of cDNA Clones Primed by Oligo(T)
      6.2.2. Genomic Cloning of p67 and the Use of Synthetic Oligonucleotides to Prime cDNA Synthesis
   6.3. DNA Sequence Analysis of p97
   6.4. Construction of a Recombinant Expression Plasmid Containing the p97 Coding Sequence
   6.5. Immunization of Mice with p97 Related Peptides
   6.6. Characterization of p97
      6.6.1. Structure of p97
      6.6.2. Homology of p97 with Transferring
      6.6.3. Function of p97
      6.6.4. Conclusion
7. Expression of Cloned p97 and Vaccine Testing
   7.1. Plasmid Expression
   7.2. Construction and Expression of Recombinant p97 Vaccinia Virus
   7.3. Recombinant p97 Vaccinia Virus is Immunogenic in Mice
   7.4. Protection and Therapy with p97 Vaccinia Virus in a Murine Tumor Model
   7.5. Recombinant p97 Vaccinia Virus is Immunogenic in Macaque Monkeys
8. Deposit of Microorganisms

1. FIELD OF THE INVENTION

The present invention is directed to vaccine formulations which can induce an immune response that selectively destroys melanoma cells in a vaccinated individual. Accordingly, a peptide or protein related to a melanoma associated antigen is produced in large quantities via recombinant DNA techniques and/or by chemical synthetic methods. The peptide or protein of the present invention can be used as an immunogen in a vaccine formulation. In certain embodiments where the peptide or protein related to a melanoma associated antigen is expressed by a recombinant virus, the recombinant virus itself may be used as an immunogen in a vaccine formulation. The invention also provides for processes which include the use of recombinant DNA techniques as well as chemical synthetic methods than enable the production of peptides or proteins related to the melanoma associated antigen in large quantities.

The invention is illustrated by way of example using as immunogens peptides related to p97, a monomeric cell surface sialoglycoprotein with an apparent molecular weight of slightly less than 97,000 daltons which is a cell surface component of melanoma cells.

2. BACKGROUND OF THE INVENTION

2.1. Tumor Associated Antigens

Work with experimental animals, particularly rodents, has shown that most tumors induced by oncogenic viruses express antigens encoded by the viral genome, and that immunization with these antigens can lead to rejection of a subsequent challenge of tumor cells induced by the same virus. Although much of this work was one with laboratory strains of virus, such as SV40, polyoma virus, and Friend, Moloney, or Rauscher murine leukemia viruses, horizontal and vertical transmission of oncogenic viruses in nature have been demonstrated; indeed a commercial vaccine against virus-induced feline leukemia an sarcoma is now available.

By contrast, a viral etiology of most human cancer has not been demonstrated. Notable exceptions are hepatitis virus (hepatoma), herpes simplex virus (cervical carcinoma), and Epstein Barr virus (nasopharyal carcinoma). However, during the past two decades it has been established that so human tumor cells express tumor antigens, i.e., antigens that distinguish the tumor cells from their normal cellular counterparts; some patients mount cell-mediated or humoral immune responses against the antigens (Hellstrom et al. 1968, Nature, 220:1352; Morton et al., 1968, Science 162: 1279-1281; Sniku et al., 1976, J. Exp. Med. 144: 873-881). Some of the targets of these immune responses are oncofetal or differentiation antigens encoded by the human genome (Hellstrom et al., 1970, Int. J. Cancer 6: 346-351).

Until recently the molecular nature of the tumor antigens was unknown, and the degree of tumor specificity of the immunological reactions was unclear. Attempts to utilize this information in developing cancer diagnostic assays or cancer therapies have been largely unsuccessful. Since spontaneous rumor regressions are extremely rare, one may also conclude that the immune responses demonstrated in vitro were ineffective in vivo; for example, while antibodies and lymphocytes obtained from a cancer patient may be effective in killing tumor cells in vitro, the immune response of the same cancer patient has no effect in vivo.

The introduction by Kohler and Milstein of the monoclonal antibody technique (1975, Nature 256: 495-497) led to intensified searches for human tumor antigens, since it provide the means to define such antigens, both at the molecular level and with respect to specificity (Hellstrom and Brown, 1979, In "The Antigens", M. Sela, ed., Academic. Press, Vol. V:1-66). Over the past several years a large number of tumor-associated antigens have been described, most of which have been defined by mouse monoclonal antibodies Reisfeld and Sell, eds., Monoclonal Antibodies and Cancer Therapy, UCLA Symposia on Molecular and Cellular Biology, New Series, Vol. 27, Alan R. Liss, Inc. New York, 1985, pp. 1-609. Although virtually all of the antigens which have been well characterized have proven to be oncofetal or differentiation antigens, at their specificity for tumors has been found to be quantitative rather than qualitative, several antigens are sufficiently specific for neoplastic versus normal cells (generally corresponding to a factor of 10 to 1,000 times) to be used as potential targets for identifying tumor cells and for therapy. Human monoclonal antibodies to tumor antigens have also been obtained (Cote et al., 1983, Proc. Natl. Acad. Sci. 80: 2026-2030). This supports the previously cited evidence that some cancer patients amount an immune reaction to their tumors.

More than half of the tumor-associated cell surface antigens so far identified are proteins or glycoproteins encoded by the human genome (rather than by endogenous or exogenous viruses), with the remainder being glycolipids, resulting from abnormal expression or regulation of glyosyl transferases.

2.2. Melanoma Associated p97 Antigen

The p97 antigen is a rumor-associated antigen that was first identified in human melanoma by using monoclonal antibodies (Brown et al., 1980, J. Biol Chem. 255:4980-4983; Dippold et al., 1980, Proc. Natl. Acad. Sci. U.S.A. 77:6114-6118; Woodbury et al., 1980, Proc. Natl. Acad. Sci. U.S.A. 77:2183-2187). The p97 antigen has been studied extensively with regard to its expression in normal and neoplastic tissues, and is present in most human melanomas and in certain fetal tissues, but is found in only trace amounts in normal adult tissues (Brown et al., 1981, J. Immunol. 127:539-546; Brown et al., 1981, Proc. Natl. Acad. Sci. U.S.A. 78:539-543; Carrigues et al., 1982, Int. J. Cancer 29:511-515). p97 has been used as a target for diagnostic imaging of melanomas in human clinical trials (Larson et al., 1983, J. Clin. Invest. 72:2101-2114).

p97 is a monomeric cell surface sialoglycoprotein, with an apparent molecular weight (MW) as measured by sodium dodecylsulfate-polyacrylamide gel electrophoresis (SDS-PAGE) of slightly less than 97,000 daltons. Monoclonal antibodies have defined three major antigenic sites which are present on a stable 40,000 dalton tryptic fragment (Brown et al., 1981, J. Immunol. 127:539-546); however, the complete sequence of p97 has not been reported. At least two other independently characterize human melanoma-associated antigens, gp95 (Dippold et al., 1980, Proc. Natl. Acad. Sci. U.S.A. 77:6114-6118) and gp87 (Khosravi et al., 1985, Int. J. Cancer 35:73-80) appear to be identical to p97 as analyzed by sequential immunoprecipitation.

The N-terminal amino acid sequence of p97 is homologous to transferring, and like transferring p97 binds iron (Brown et al., 1982, Nature, London, 296:171-173). Analysis of somatic cell hybrids and in situ hybridization has shown that the p97 gene, like the genes for transferrin and transferrin receptor, is located on chromosomal region 3q21-3q29 (Plowan et al., 1983, Nature, London, 303:70-72; Yang et al., 1984, Proc. Natl. Acad. Sci. U.S.A. 81:2752-2756). These observations suggest that p97 plays a role in iron metabolism.

2.3. Cancer Vaccines

Studies in experimental animals, usually mice, have shown that immunization with living or killed cancer cells can lead to rejection of a subsequent challenge of viable cancer cells. Attempts to immunize with cell-free material have generally been less successful, but some successes have been reported. (For a review see Hellstrom an Brown, 1979, in *The Antigens*, M. Sela ed. Academic Press, Vol. V:1-66). In many cases the target antigens responsible for the protective effects have been virally encoded, but in many other cases the nature of the antigen which elicits a protective immune response is unknown.

Studies in humans are much more difficult, and the effectiveness of cancer vaccines is disputed, in spite of some reports of success. In many cases the vaccine preparations have consisted of irradiated tumor cells or tumor cells killed by exposure to certain chemical agents. Because pure human tumor-associated antigens have not been available there are no reports of their use in vaccines.

A major theoretical objection to the proposed use of cancer vaccines in humans is that humans who are "vaccinated", for example, with killed cancer cells or cell-free preparations, will be immunologically unresponsive because the tumor antigens that may be the targets of the immune response are present, albeit in trace amounts only, in some normal cells and will thus be perceived by the immune system as "self". Most, if not all, tumor-associated antigens detected in human tumors by monoclonal antibodies are also present in some normal tissues, and there is little evidence that cancer patients respond to them effectively in vivo. There is evidence that suppressor cells play a major role in down-regulating the immune response to tumor antigens (Nepom et al., 1983, Experientia, 39:235-242). Furthermore, a suppressor cell response induced by one set of tumor antigens may prevent the induction of an effective tumor-destructive response to another set of tumor antigens, which by themselves would not induce suppression (Hellstrom et al., 1983, in Biomembranes, A. Nowotny ed., Plenum Press, pp.365-388).

2.4. Recombinant DNA Techniques and Vaccinia Virus

The use of recombinant DNA technology for the production of subunit vaccines to protect against infections involves the molecular cloning and expression in an appropriate vector of generic information coding for proteins which can elicit an immune response against the protein in the host animal. Recently, a novel approach has been described which is potentially useful in the production of subunit vaccines (Mackett et al., 1982, Proc. Natl. Acad. Sci. 79:7415-7419; Mackett et al., 1984, J. Virol. 49: 857-864; Panicali, D. and Paoletti, E., 1982, Proc. Natl. Acad. Sci. 79: 4927-4931). This approach involves the use of vaccinia virus as a vector to express foreign genes inserted into its genome. Upon introduction into host animals, the recombinant vaccinia virus expresses the inserted foreign gene and thereby elicits a host immune response to such gene products. Since live recombinant vaccinia virus can be used as a vaccine, this approach combines the advantages of both subunit and live vaccines.

Vaccinia virus contains a linear double-stranded DNA genome of approximately 187 kilobase pairs and replicates within the cytoplasm of infected cells. These viruses contain a complete transcriptional enzyme system (including capping, methylating and polyadenylating enzymes) within the virus core that are necessary for virus infectivity. Vaccinia virus transcriptional regulatory sequences (promoters) allow for initiation of transcription by vaccinia RNA polymerase but not by host cell RNA polymerase.

Expression of foreign DNA in recombinant vaccinia viruses requires the ligation of vaccinia promoters to protein-coding DNA sequences of the foreign gene. Plasmid vectors, also called insertion vectors, have been constructed to insert chimeric genes into vaccinia virus. One type of insertion vector is composed of: (a) a vaccinia virus promoter including the transcriptional initiation site; (b) several unique restriction endonuclease cloning sites located downstream from the transcriptional start sire for insertion of foreign DNA fragments; (c) nonessential vaccinia virus DNA (such as the TK gene) flanking the promoter and cloning sites which direct insertion of the chimeric gene into the homologous nonessential region of the virus genome; and (d) a bacterial origin of replication and antibiotic resistance marker for replication and selection in E. coli. Examples of such vectors are described by Mackett (Mackett et al., 1984, J. Virol. 49: 857-864).

Recombinant vaccinia viruses are produced by transfection of recombinant bacterial insertion plasmids containing the foreign gene into cells previously infected with vaccinia virus. Homologous recombination takes place with the infected cells and results in the insertion of foreign gene into the viral genome. The infected cells can be screened using immunological techniques, DNA plaque hybridization, or genetic selection for recombinant viruses which subsequently can be isolated. These vaccinia recombinants retain their essential functions and infectivity and can be constructed to accommodate approximately 35 kilobases of foreign DNA.

Foreign gene expression can be detected by enzymatic or immunological assays (for example, immunoprecipitation, radioimmunoassay, or immunoblotting). Naturally occurring membrane glycoproteins produced from recombinant vaccinia infected cells are glycosylated and may De transported to the cell surface. High expressing levels can be obtained by using strong promoters or by cloning multiple copies of a single gene.

3. SUMMARY OF THE INVENTION

Vaccine formulations are described which may be used to induce an immune response that selectively destroys melanoma cells in vaccinated individuals. More specifically, the vaccine formulations of the present invention comprise an immunogen that induces an immune response directed against a melanoma associated antigen such as the melanoma associated p97 antigen. According to the invention, a number of vaccine formulations are possible. For example, the immunogen of a "subunit vaccine" of the present invention comprises a peptide or protein related to p97 which may be formulated with an appropriate adjuvant. Such peptides or proteins comprise amino acid sequences derived from all or a portion of the amino acid sequence of p97 substantially as depicted in FIG. 3 including but not limited to altered amino acid sequences in which functionally equivalent amino acid residues are substituted for residues within the sequence resulting in a silent change, and/or modified or processed amino acid sequences, as for example, glycosylated amino acid sequences, phosphorylated amino acid sequences, etc. or chemically modified amino acid sequences. Hereinafter, the peptides or proteins of the present invention which are related to the melanoma associated p97 antigen whether altered, unaltered, modified or unmodified, will be referred to as "p97 related peptides". Where the p97 related peptide is a hapten (i.e., antigenic but not immunogenic) the hapten can De conjugate to a carrier molecule that confers immunogenicity.

The p97 related peptides of the invention may be produced using recombinant DNA techniques and/or chemical synthetic methods. When p97 related peptides are chemically synthesized such synthetic p97 related peptides can comprise those amino acid sequences derived from regions of p97 that are expected to be antigenic (Hopp and Woods, 1981, Proc. Natl. Acad. Sci. U.S.A., 78:3824-3828). Where the p97-related peptides of the present invention are produced by using recombinant DNA techniques, a nucleotide sequence which encodes the whole or a portion of p97 is inserted into a recombinant expression vector such as a virus or a plasmid which, in an appropriate host, can direct the expression of a p97 related peptide that can be purified from the culture medium. The nucleotide sequence inserted is derived from all or portions of the p97 sequence substantially as depicted in FIG. 3 including but not limited to nucleotide sequences in which functionally equivalent nucleotide codons are substituted for codons within the sequence resulting in a silent change; in other words, different codons which encode the same amino acid or its functional equivalent may be substituted within the sequence depicted in FIG. 3. When a plasmid expression vector is used, one that is suitable for expression in eukaryotic cells is preferred, but a prokaryotic expression vector may also be used In another embodiment of the invention where the expression vector is a recombinant virus, a vaccine may be formulated as a viral vaccine, in which case the immunogen comprises the recombinant virus that expresses a p97 related peptide. Depending upon the nature of the recombinant virus used as the immunogen, either an inactivated virus vaccine or a live virus vaccine may be formulated. Appropriate immunization with the vaccine formulations of the present invention can result in the induction of an immune response which leads to the destruction of melanoma cells in the immunized subject.

The invention also describes a system in which the vaccine formulation can be tested and outlines how the test should be performed. For example, the vaccine formulations can be evaluated for efficacy in animal models, initially rodents, then in non-human primates, and finally in humans, preferably in patients who are in remission but have a high probability of recurrence due to micrometastases.

4. BRIEF DESCRIPTION OF THE FIGURES

FIGS. 1A and 1B represents an autoradiograph of the cell-free translation products of p97 mRNA resolved by SDS-PAGE. In FIG. 1A, lane 1 represents the translation products of p97 enriched mRNA, whereas lane 2 represents the translation products of unenriched mRNA, each derived from 0.5 μl total translation products of 5 ng mRNA. In FIG. 1B, lane 1 represents the translation products of p97 enriched mRNA whereas lane 2 represents the translation products of unenriched mRNA, each derived from 5 μl translation products of 5 ng mRNA immunoprecipitated with anti-p97 serum.

Figure 2:
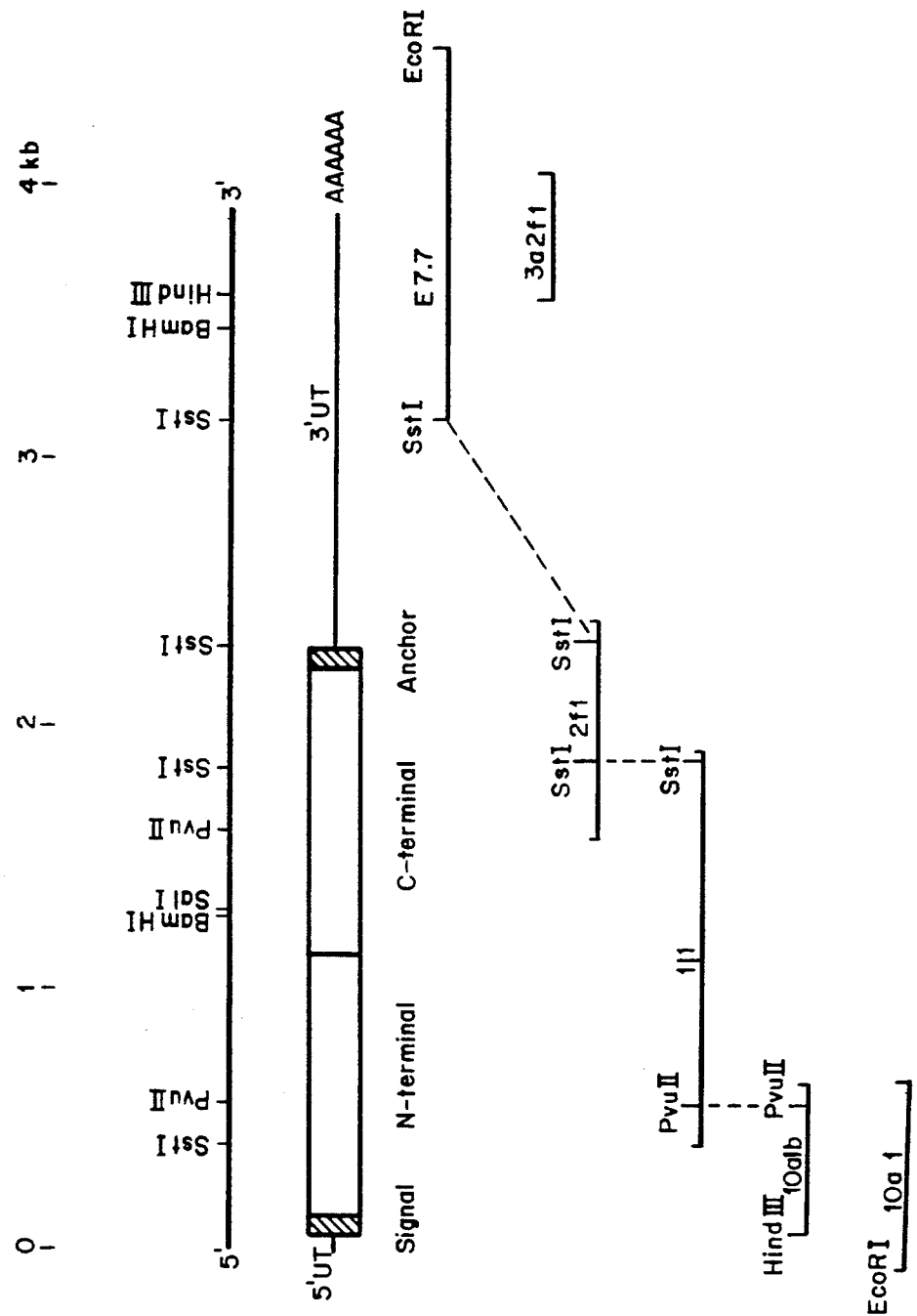
Figure 2A:
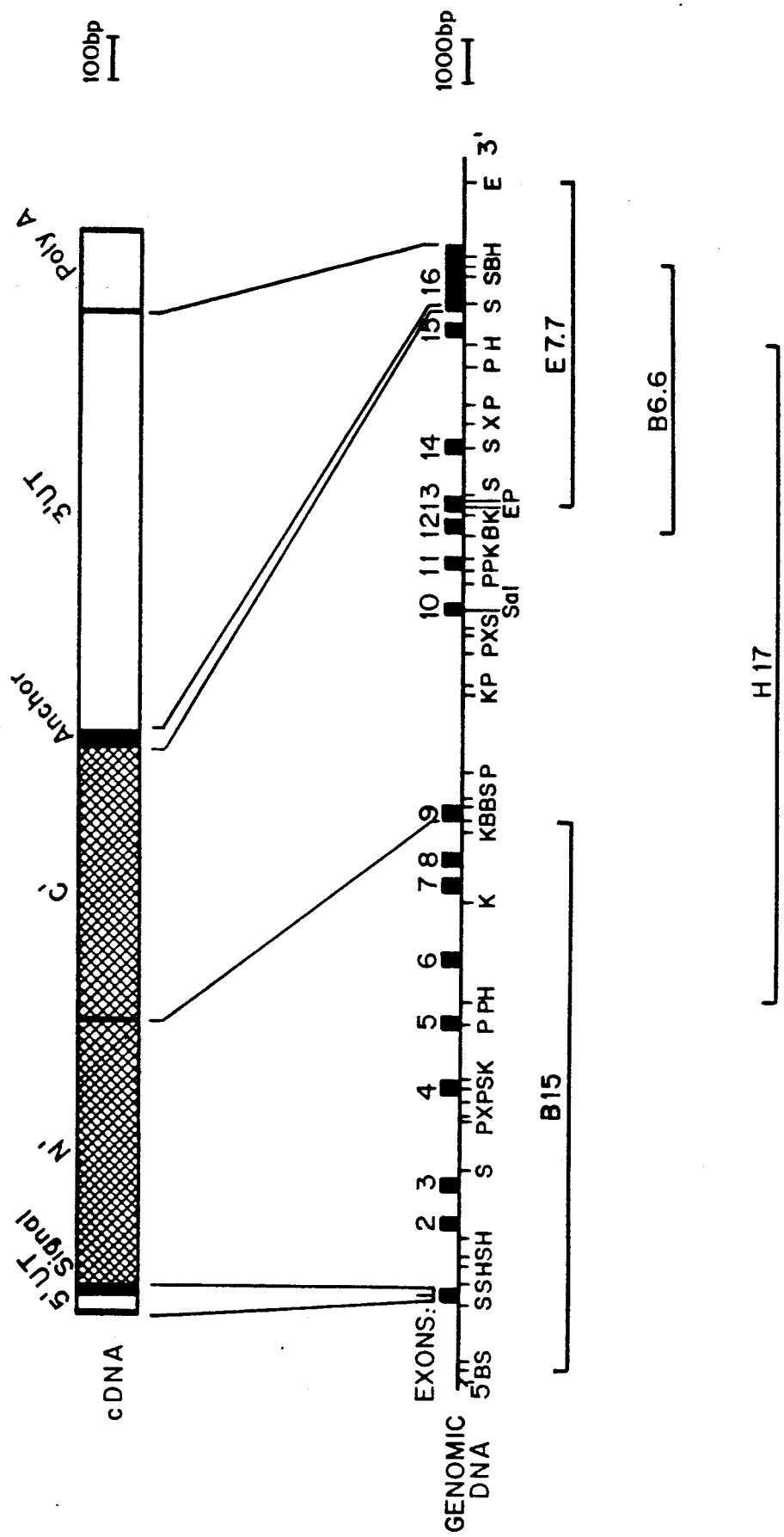

FIG. 2 and 2A are diagrammatic representations of the structure of p97 mRNA. The arrangement of the coding region (from the signal sequence to the anchor sequence) and the non-coding region (3'UT) as well as the duplicated domain structure of the p97 precursor (open bar) is indicated. The location of various restriction enzyme recognition sequences are indicated above the mRNA. The relative positions of four cDNA clones are indicated below the mRNA structure. The cDNA clone p97-3a2f1 (3a2f1) was isolated from a cDNA library in which the cDNAs were transcribed on oligo(T)-primed p97-enriched mRNAs and cloned in pBR322; whereas, cDNA clones p97-2f1 (2f1), p97-1j1 (1j1), and p97-10a1 (10a1) were isolated by priming cDNA synthesis with oligonucleotides that encode p97 exon sequences and cloning the resulting cDNA fragments into lambda-gt10. FIG. 2A is a diagrammatic representation of genomic clones B15, H17, B6.6 and E7.7 which were cloned in lambda L47.1.

Figure 3A:
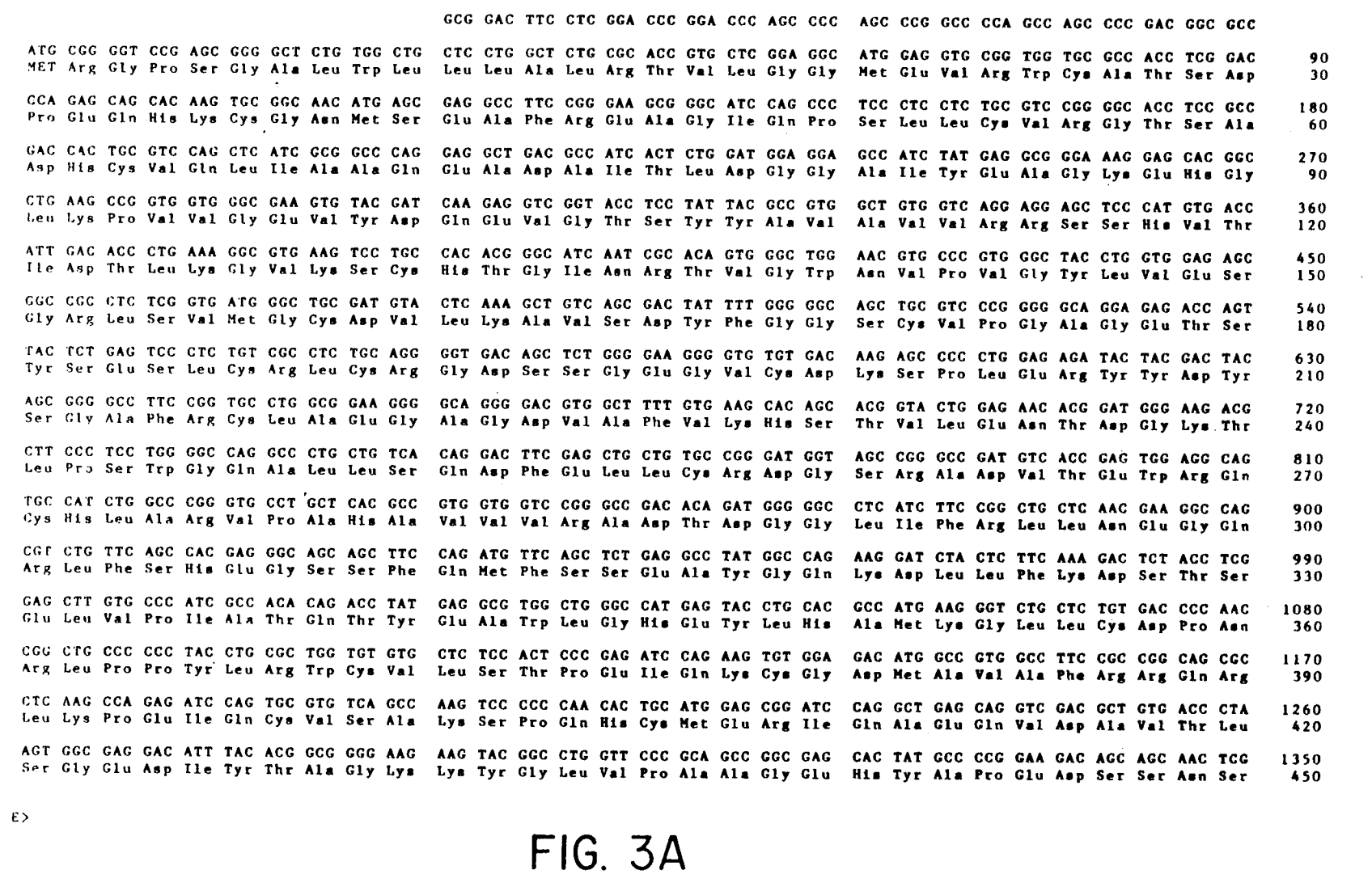

FIGS. 3A and 3B represent the nucleotide sequence of human p97 precursor cDNA and its deduced amino acid sequence. The N-terminal amino acid residues determined previously by protein sequencing were identical to those predicted from the nucleotide sequence (amino acid residue numbers 21-30). The potential glycosylation sites at amino acid residues 38, 135 and 515 (open bar) and the membrane anchor region at the C-terminus (solid bar) are indicated. One polyadenylation signal (AATAAA indicated in a box) was detected at position 3847, which is 50 base pairs upstream of a polyadenylated tract.

Figure 4:
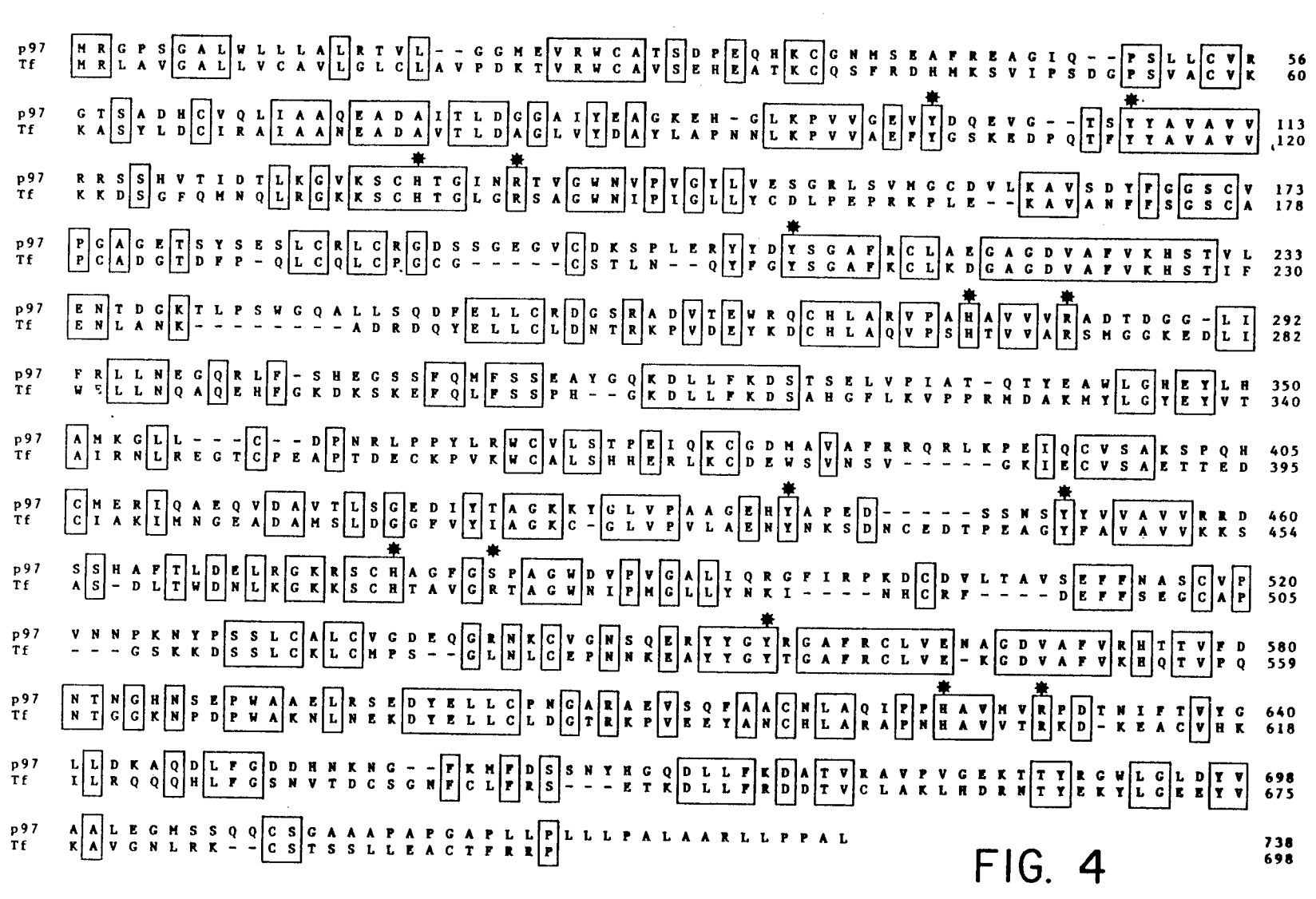

FIG. 4 represents a comparison of the predicted amino acid sequences of the p97 precursor and that of human serotransferrin (Yang et al., 1984, Proc. Natl. Acad. Sci. U.S.A. 81:2752-2756; Davis et al., 1985, J. Mol. Biol. 181:111-121). Conserved residues have been boxed. Tyrosine, histidine and arginine residues implicated in iron binding of transferrin (Metz-Boutigue et al., 1984, Eur. J. Biochem. 145:659-676) are indicated by asterisks (*).

Figure 5:
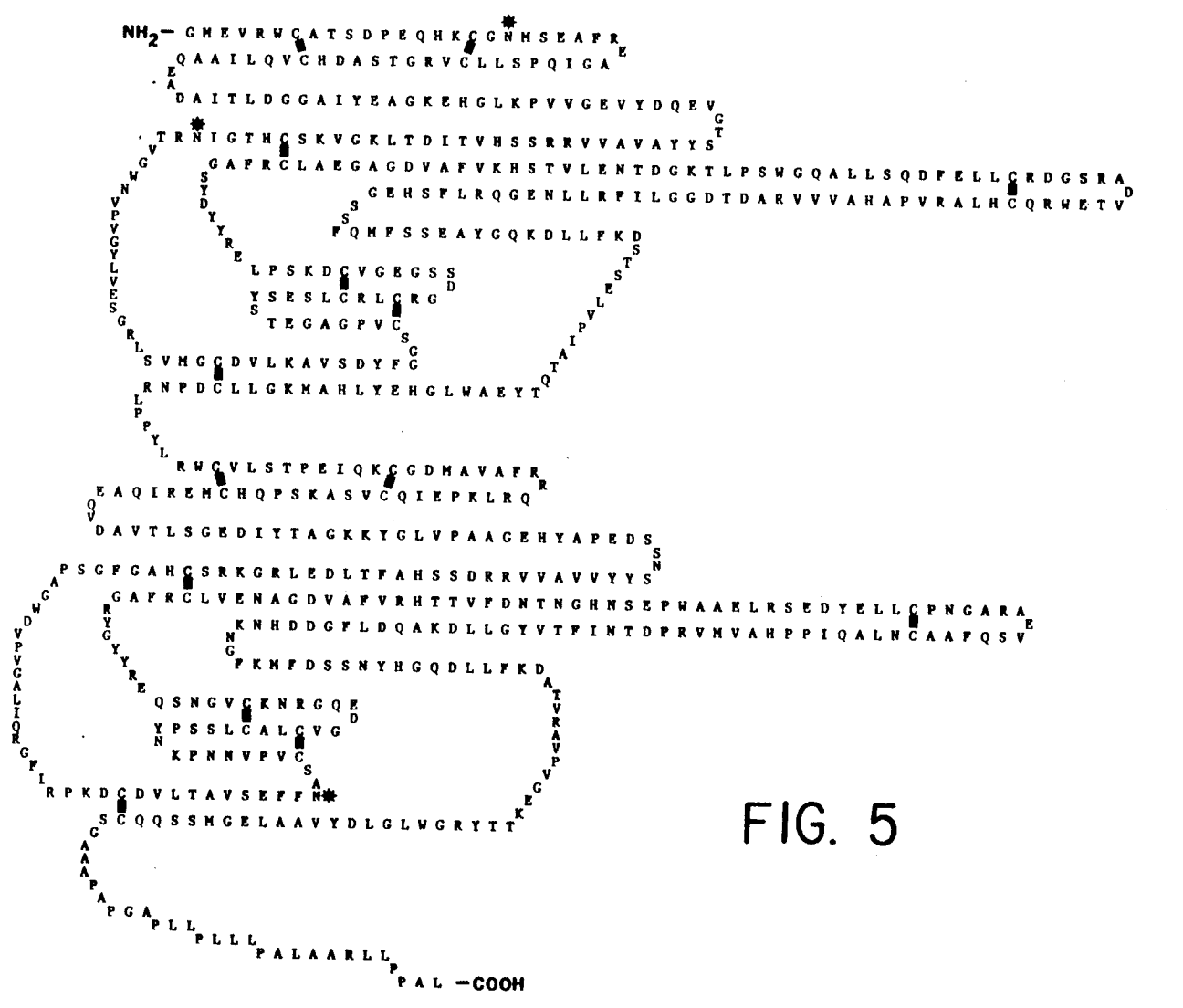

FIG. 5 is a diagrammatic representation of a two-dimensional model of the structure of p97 based upon the presence of cysteine residues conserved between the transferrin superfamily members. The three potential glycosylation sites are indicated by asterisks (*). The hydrophobic membrane anchor domain is apparent at the C-terminus of p97 (COOH).

Figure 6:
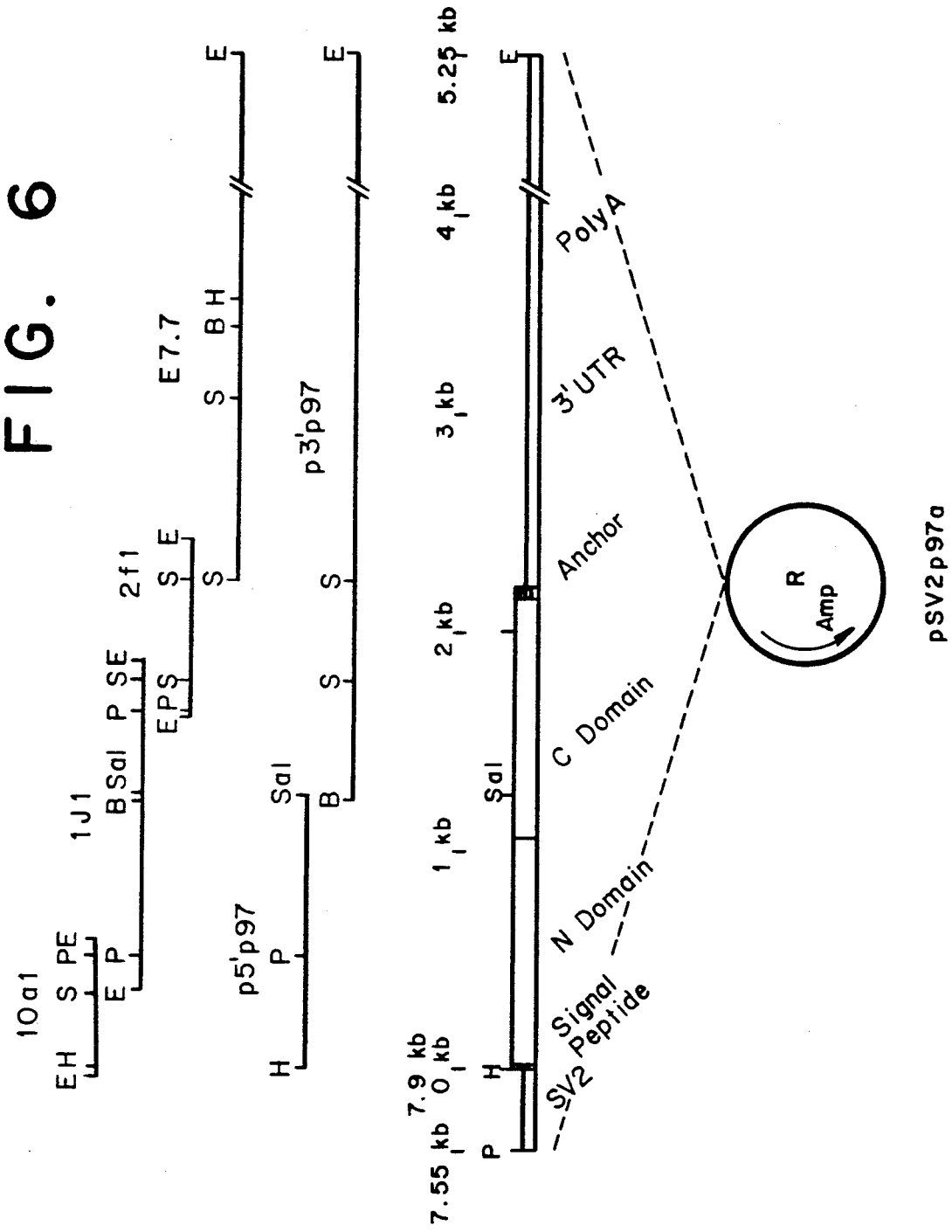

FIG. 6 is a diagrammatic representation of the genetic structure of: the p97 cDNA clones and fragment of genomic clone lambda E7.7 used for construction of the p97 expression vector; and the pSV2p97a expression vector. The following abbreviations are used: E, EcoRI; P, PvuII; Sal, SalI; S, SstI; B, BamHI.

Figure 7A:
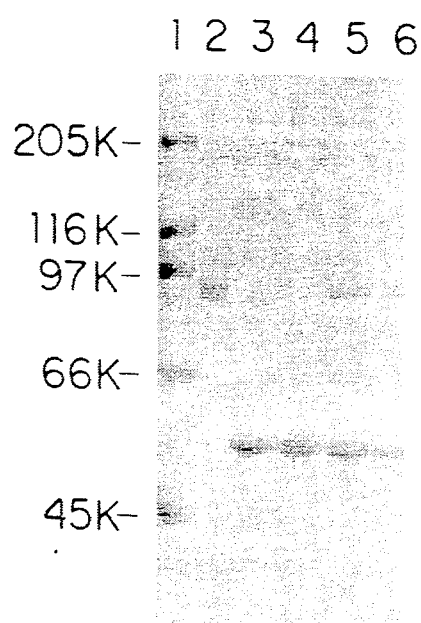
Figure 7B:
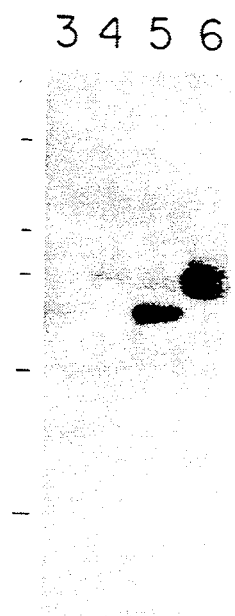

FIGS. 7A and 7B show the results of gel electrophoresis in the characterization and immunopurification of recombinant p97 protein. A transfected CHO clone (CHO3+) and SK-MEL 28 human melanoma cells were labeled with $^{35}$S-cysteine in the presence (+TM) or absence (−TM) of tunicamycin (TM). Cells were seeded into 100 mm$^2$ plates and allowed to reach near confluency. Medium was removed and replaced with 3 ml cysteine-free medium with or without addition of 1 ug/ml tunicamycin. After 30 minutes at 37° C. 250 uCi per ml L-$^{35}$S-cysteine (1016 Ci per mmol; New England Nuclear) was added for a further 6 hours. Harvesting of cells, preparation of cell lysates, immunoprecipitation, and SDS-PAGE were as described supra. Extracts were immunoprecipitated with p97-specific antibodies, and proteins were analyzed by SDS-polyacrylamide gel electrophoresis (SDS-PAGE). (7A), Coomassie blue stained SDS-polyacrylamide gel. Lane 1, protein markers; lane 2, immunopurified p97 shed from transfected mouse B16 cells; lane 3, SK-MEL 28 cells +TM; lane 4, SK-MEL 28 cells −TM; lane 5, CHO3+ cells +TM; lane 6, CHO3+ cells −TM. (7B) Autoradiogram of the same gel as in (7A).

Figure 8:
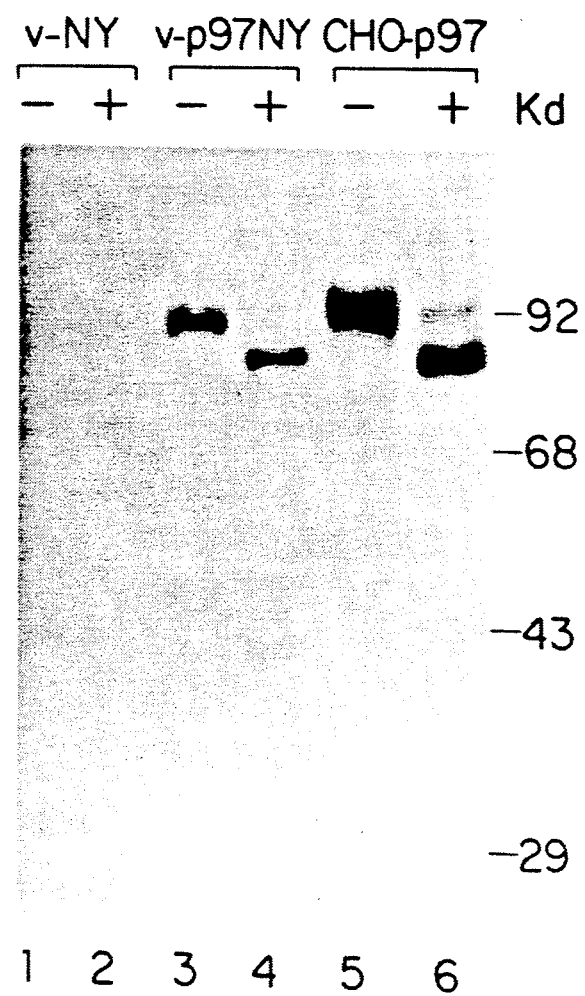

FIG. 8 shows the results of radioimmunoprecipitation of expressed p97 in transfected cells or Vp97a-NY infected cells. BSC cells were infected overnight with wild type vaccinia virus or p97 recombinant vaccinia virus. These viruses or the transfected cell line CHO-p97.A were incubated with $^{35}$S-labeled methionine and cysteine with or without tunicamycin at 2 ug/ml (Sigma). The cells were lysed six hours later, precipitated with monoclonal antibody 96.5, and separated by electrophoresis on a 10% polyacrylamide gel. The gel was autoradiographed overnight. The tunicamycin treated group is on the right for each group.

Figure 9:
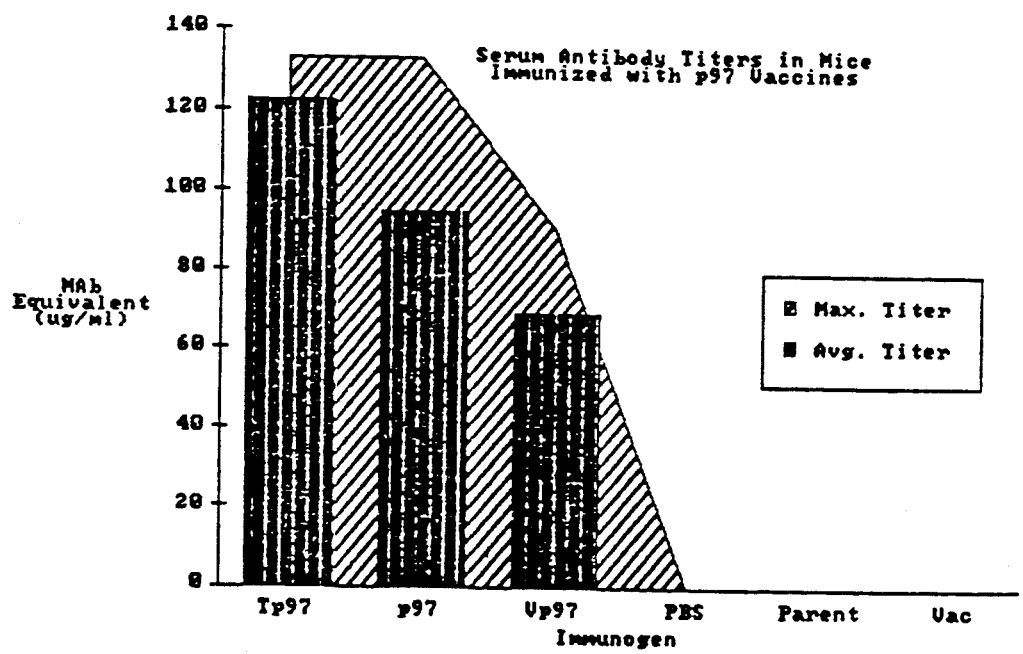

FIG. 9 depicts the serum antibody titers in mice immunized with p97 vaccines. Tp97 represents five mice immunized with 5 x 10$^6$ irradiated M2svp97a.A cells (syngeneic tumor cells transfected and expressing surface p97) in complete Freund's adjuvant, and boosted with the same number of cells in phosphate-buffered saline. p97 is a group of five mice immunized with 100 ug purified p97 protein in complete Freund's adjuvant, and boosted with 50 ug aqueous protein. Vp97 is a group of five mice immunized and boosted with 10$^7$ plaque forming units of Vp97a-NY by tail scarification.

Figure 10:
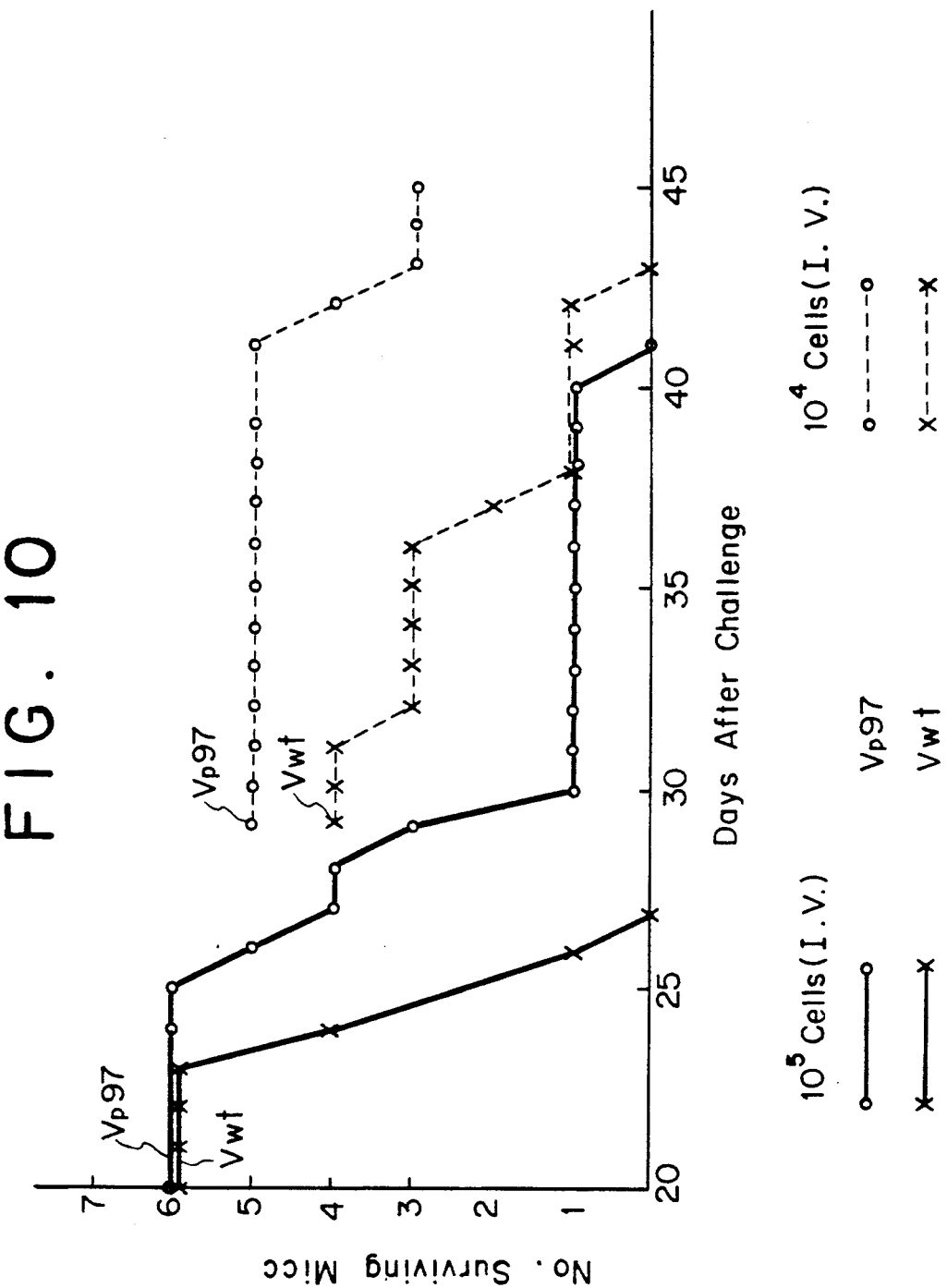

FIG. 10 depicts the therapeutic effect of vaccination of tumor-challenged mice with a recombinant p97 vaccinia virus (Vp97a-NY). Mice were challenged with 10$^5$ or 10$^4$ p97-expressing tumor cells (M2SVp97a.E) intravenously. Two days later, mice were inoculated by tail scarification either with Vp97a-NY or Vwt-NY. Weekly inoculations by tail scarification were repeated, and mouse survival recorded.

5. DETAILED DESCRIPTION OF THE INVENTION

The present invention is directed to the production of vaccines for the prevention or treatment of melanomas It is based upon the observation that melanomas have tumor-associated cell surface antigens, such as the p97 antigen, which are present in greater amounts in the melanoma cells than they are in normal tissues. According to the present invention, peptides or proteins related to the melanoma associated p97 antigen (i.e., p97-related peptides) are produced using recombinant DNA techniques and/or chemical synthetic techniques. The p97-related peptides of the present invention comprise amino acid sequences derived from whole or portions of the amino acid sequence of p97 substantially as depicted in FIG. 3. These include amino acid sequences derived from FIG. 3 which have been altered by the substitution of one or more amino acid residues within the sequence by another amino acid of a similar polarity which acts as a functional equivalent thus resulting in a silent alteration. Substitutes for an amino acid within the sequence may be selected from cimer members of the class to which the amino acid belongs. For example, the nonpolar (hydrophobic) amino acids include alanine, leucine, isoleucine, valine, proline, phenylalanine, tryptophan, and methionine. The polar neutral amino acids include glycine, serine threonine, cysteine, tyrosine, asparagine, and glutamine. The positively charged (basic) amino acids include arginine, lysine, and histidine. The negatively charged (acidic) amino acids include apartic acid and glutamic acid. Moreover, the p97 related peptides of the present invention, whether or not altered by the substitution f amino acid residues, may be further modified or processed by glycosylation, phosphorylation, etc. or by chemical modifications. These p97 related peptides can be used as immunogens in vaccine formulations that elicit an immune response directed against melanoma cells present in the vaccinated patient.

According to one embodiment of the present invention, recombinant DNA techniques are used to insert nucleotide sequences encoding the p97 antigen into expression vectors that will direct the expression of the p97 related peptides in appropriate host cells. The nucleotide sequences encoding the p97 antigen comprise nucleotide sequences derived from whole or portions of the p97 nucleotide sequence substantially as depicted in FIG. 3. Due to the degeneracy of the DNA code for amino acids, (i.e., most amino acids can be encoded by more than one codon) functionally equivalent codons (i.e., different codons which encode the same amino acid or its functional equivalent) may be substituted within the p97 sequence depicted in FIG. 3 provided the substitution results in a silent change. The expression vector-host cell systems which contain a nucleotide sequence encoding all or part of p97 can be used to produce large amounts of pure p97 related peptides in vitro in which case the gene products can be purified from the cells in culture and used as immunogens in subunit vaccine formulations. Purification of the p97 related peptide may be accomplished using a variety of biochemical methods, including immune affinity purification using monoclonal antibodies. In addition, purification of the p97 related peptide can be facilitated by modifying the DNA sequences that encode the p97 related peptides so that the sequences responsible for anchoring the protein in the plasma membrane are remove yet the sequence responsible for transporting the protein to the cell membrane are not removed, so that a truncated antigenic molecule is secreted into the culture medium by the host cell. In the case of p97 related peptides produced by prokaryotic cells, lack of appropriate postranslational modifications may result in an antigenically inactive product, which may have to De activated by appropriate chemical or other treatments.

In certain embodiments, where the expression vector is a virus, the virus itself can be formulated as a vaccine. In such cases inactivated recombinant virus vaccines can be prepared. Where the expression vector is an infectious recombinant viruses that does not cause disease in the host either an inactivated viral vaccine or a live virus vaccine preparation which provides for substantial immunity can be formulated. A particularly useful expression vector for this purpose is a recombinant vaccinia virus which expresses the p97 related peptides of the present invention. To this e: a nucleotide sequence coding for all or part of the p97 antigen can be inserted into a vaccinia virus vector that is capable of directing the expression of the sequence in a appropriate host. The invention includes the use of other virus expression vectors as vaccines, more particularly, adenoviruses.

In another embodiment of the present invention, the deduced amino acid sequence of p97 may be be examined for sequences with properties, particularly hydrophilicity, that are predictive of the presence of that sequence at the surface of the protein molecule and of its probable antigenicity and/or immunogenicity. These p97 related peptides may be chemically synthesized and used as immunogens in vaccine formulations.

The invention also provides a method for producing p97 related peptides that may be used for purposes other than vaccine production. The p97 related peptide may be used to immunize animals so as to produce antisera or monoclonal antibodies specific for the melanoma cells of interest. These may be used as a component in a diagnostic assay, or for the affinity purification of radiolabeled rug-linked, or toxin-linked antibodies to be used for cancer therapy.

The invention is demonstrated by way of the examples in which we describe the construction of a p97-based vaccine against human melanoma. However, the methods and compositions described herein are not limited to the construction of vaccines using p97, but can be applied to other tumor-associated antigens.

The invention is presented as follows, solely for the purpose of clarity of description: (a) the nucleotide and amino acid sequence of p97; (b) p97 related peptides prepared by chemical synthetic methods; (c) p97 related peptides produced by expression vector-host systems; (o) immunological characterization of the p97 reared peptides; and (e) formulation of vaccines.

5.1. Sequence Analysis of the Melanoma Associated p97 Antigen

The nucleotide sequence of the gene coding for p97 and its derived amino acid sequence are depicted in FIG. 3. Functionally equivalent sequences are within the scope of the present invention. These include out are not limited to nucleotide sequences comprising all or portions of the nucleotide sequence depicted in FIG. 3 which are altered by the substitution of different codons that encode the same or a functionally equivalent amino acid residue thus producing a silent change as well as amino acid sequences comprising all or portions of the amino acid sequence depicted in FIG. 3 which are altered by the substitution of functionally equivalent amino acid residues within the sequence thus producing a silent change and derivatives thereof which are modified or processed, for example by glycosylation, phosphorylation, etc. or by other chemical modifications.

The subsections below describe the strategy that was used to determine the sequence of p97 as depicted in FIG. 3 as well as alternate techniques that could be used to determine the sequence of p97 or other tumor antigens that would be useful in vaccine formulations.

5.1.1. Identification and Characterization of the Melanoma Associated p97 Antigen The activity and amino acid sequence of the melanoma associated p97 antigen was not known; as a result, identification of the p97 antigen was accomplished using monoclonal antibodies directed against p97. A number of techniques may be used to generate monoclonal antibodies specific for p97. For example, the hybridoma technique developed by Kohler and Milstein (1975, Nature 250:495-497) may be used as follows: mice or rats are immunized with human melanoma cells and lymphocytes collected from the immunized animals are fused with myeloma cells; alternatively, lymphocytes from melanoma patients can be fused with myeloma cells (Cote, et al., 1983, Proc. Natl. Acad. Sci. 80:2026; Haspel et al., 1985, Cancer Res. 45:3951), or the technique for producing monoclonal antibodies using Epstein-Barr virus (Cole et al., 1985, The EBV-Hybridoma Technique and its Application to Human Lung Cancer, in Monoclonal Antibodies and Cancer Therapy, Alan R. Liss, Inc., pp: 77-96) can be used to generate monoclonal antibodies directed against p97. In any case, the resulting hybridomas are screened for the production of antibodies that bind to the melanoma cells out do not bind to normal cells.

The monoclonal antibodies directed against p97 described above can be used in a number of ways to facilitate the identification, characterization, cloning and expression of nucleotide sequences which allow for the production of peptides and proteins related to the p97 antigen, in large quantities. For example, the monoclonal antibodies may De used to further characterize the p97 antigen by radiolabeled: all the proteins made by the tumor cell, immunoprecipitating the tumor protein with the monoclonal antibody used to identify the p97 antigen, and fractionating the immunoprecipitated proteins by gel electrophoresis. Protein antigens are identified as distinct bands on the resulting autoradiograph (Brown et al., 1980, J. Biol. Chem. 255:4980-4983). In addition, the monoclonal antibodies directed against p97 can be used to facilitate cloning: as follows: (a) to immunopurify polysomes in order to identify and obtain mRNA transcripts present in the melanoma cell which encode the p97 antigen; (b) to identify clones in a cDNA expression library that express peptides or proteins related to the p97 antigen; (c) to purify the p97 antigen in order to prepare additional monoclonal antibodies or antisera for use in the previous two applications; or (c) to identify cells into which the gene for the p97 antigen has been introduced by transfection.

The monoclonal antibodies can also be used to facilitate structural and immunochemical characterization of the p97 antigen, so as to identify extracellular and antigenic domains of the molecule, an to purify the molecule for amino acid sequence analysis (Brown et al., 1981, Proc. Natl. Acad. Sci. U.S.A. 78:539-543; Brown et al., 1982, Nature, London, 296:171-173).

Further characterization of p97 involves determination of cellular localization and mapping antigenic determinants an functional contains. Subcellular localization can be determined by immunofluoresence microscopy and by cellular fractionation experiments. Antigens such as p97 that are present on the cell surface are preferred for vaccine construction, although intracellular antigens may also be useful. If multiple monoclonal antibodies are available, antigenic determinants can be mapped by competition experiments, in which each antibody is radiolabeled and tested for competition with each of the other antibodies. Domains of the a molecule can be identified by limited digestion with proteases followed by SDS-PAGE. Together these data should allow identification of regions of the molecule that are most immunogenic. If the a monoclonal antibodies were obtained by immunization with intact cells, then these regions of the molecule are most likely to be extracellular and to be useful for vaccine construction.

Amino acid sequence analysis allows unambiguous identification of the protein and its comparison with other proteins (Brown, et al., 1982, Nature, London, 296:171-173). If the protein comprises more than 50 amino acid residues, it may De feasible to determine only a part of the amino acid sequence, most often the N-terminus. Protein antigen for amino acid sequencing can be purified from cell lysates by immunoaffinity chromatography with the monoclonal antibody, followed by preparative SDS-PAGE. The N-terminal amino acid sequence of the purified protein is then determined by using an automatic amino acid sequencer, preferably a gas-phase machine for greatest sensitivity.

5.1.2. Identification, Cloning and Sequencing of DNA Coding for the Melanoma Associated p97 Antigen Early cloning studies concentrated on abundant proteins such as globin and ovalbumin, whose mRNAs often comprised 10 to 50% of total m:RNA. These m:RNAs could be purified to homogeneity by size fractionation, and pure cDNA probes were used to screen libraries of a few hundred clones by colony hybridization. For proteins whose mRNAs comprise 1 of 10% of total mRNA, differential hybridization with two cDNA probes can be used, in which o: of the cDNA probes contains the sequence of interest, and the other is a negative control. Messenger RNAs coding for low-abundance proteins, such as tumor-associated antigens, which may comprise as little as 0.01% of cellular A, are much more difficult to clone, because tens of thousands of clones must be screened, and cDNA probes will not give a specific hybridization signal. Both problems can be alleviated by enriching the mRNA for the sequence of interest.

Several approaches used to clone DNA coding for human melanoma associated p97 antigen are described below. The resulting clones were analyzed in order to identify a clone or clones that spanned the entire cooing region of p97. The p97 nucleotide inserts of the clones so identified can then be sequenced by any method known in the art. The various approaches are described in more detail below.

(a) ISOLATION OF mRNA BY POLYSOME IMMUNOPURIFICATION

In this technique, polysomes (which consist of mRNA, ribosomes and nascent polypeptide chains) are purified by immunoaffinity chromatography with antibodies that recognize antigenic determinants present on the nascent chains. In many cases monoclonal antibodies obtained by immunization with intact cells or cell extracts recognize the antigens in their native conformations, but they may not be appropriate for polysome immunopurification, since there is a significant chance that the antigenic determinants recognized may not be present in nascent chains. Since translation starts at the N-terminus of the polypeptide, epitopes close to the C-terminus are likely to be absent from the majority of the nascent chains. This problem is avoided either by using antibodies than recognize N-terminal epitopes, or by preparing polysomes from cells treated with a protein synthesis inhibitor that blocks termination.

A more serious problem is that mature proteins differ from nascent chains because of post translational modifications. This problem is particularly acute for cell surface proteins, which are modified more extensively by removal of the signal peptides, addition of carbohydrate side chains, and formation of disulfide bridges. If a polyclonal antiserum is used for polysome immunopurification, the differences in antigenicity between nascent chains and the mature protein may be of little consequence, since during immunization the rabbit or other animal is exposed not only to the native protein but also to partially or completely denatured forms, particularly if Freund's adjuvant has been used. Even if these antibodies represent only a minor fraction of the antibody population there may still be enough present to bind the nascent chains. Unfortunately, preparation of a polyclonal antiserum to a low-abundance proteins may be extremely difficult. Although a monoclonal antibody may be used to purify the antigen for further immunizations, each gram of cultured cells often yields only a microgram of antigen. This is enough to immunize several mice, but barely sufficient for a single rabbit.

Another solution to the problem is to obtain a monoclonal antibody that recognizes antigenic determinants present in nascent chains by using denatured p97 antigen as the immunogen used to prepare the monoclonal antibody. In the example of the present invention a panel of monoclonal antibodies that recognized three distinct epitopes on the N-terminal 40,000 dalton molecular weight domain of the p97 molecule were available, and we used a pool of monoclonal antibodies each with a different specificity in the hope that one or more of them would bind to nascent chains. The antibodies chosen were highly specific for p97, in that each of them immunoprecipitated a single band of p97 from a radiolabeled whole cell lysate, and they had high binding affinities. For the cloning project we chose three IgG2a antibodies, one specific for each of the three epitopes. In general the chance of success may be increased by using a number of antibodies to distinct epitopes.

When using monoclonal antibodies the question remains of how one can predict whether a given monoclonal antibody or combination of antibodies will recognize the nascent chains and thus be suitable for use in polysome immunopurification. One approach is to determine whether the monoclonal antibody immunoprecipitates antigen that has been translated in the reticulocyte lysate system, relying on the assumption that the in vitro translation product, not being processed, will resemble the nascent chains. An alternative approach is to proceed with the polysome immunoprecipitation on a small scale and then to use in vitro translation to determine whether the mRNA species of interest has been enriched.

When the polysome immunopurification technique is used it is important to monitor the purification by measuring mRNA activity. This can be done by translating the mRNA in a reticulocyte lysate system and analyzing the translation products by SDS-PAGE. Although the tumor-associated antigen may be too minor a component of the translation products of unenriched mRNA to be seen among the hundreds of more abundant species, it should be detectable in the translation products derived from the enriched mRNA samples. Alternatively the Xenopus oocyte translation system can be used, if a sensitive immunoassay is available to detect the translated tumor-associated antigen. For p97 a highly sensitive double determinant immunoassay (DDIA), which employs two monoclonal antibodies specific for two different epitopes of p97, was used for this purpose.

Protein A bound to Sepharose can be used for the polysome immunopurification. The protein A adsorbent has two applications in this procedure. The first is to purify the monoclonal antibodies from the crude ascites fluids, thereby removing contaminating ribonuclease activity. The protein A adsorbent is then used in conjunction with the purified antibodies to immunopurify polysomes bearing the specific nascent chain.

Translation of the mRNA in a reticulocyte lysate system allows the biochemical characterization of the translation product as well as an assessment of its purity.

(b) OLIGONUCLEOTIDE PROBES

Another method that may be used in accordance with the invention to clone the cDNA coding for a tumor-associated antigen such as p97 is to determine a partial or complete amino acid sequence of the antigen and to synthesize an oligonucleotide probe based on the nucleotide sequence deduced from the amino acid sequence. The oligonucleotide may then be used as a primer for cDNA synthesis and as a probe to screen the resulting cDNA library. Accordingly, the melanoma associated p97 protein may conveniently be purified from lysates of melanoma cells by affinity chromatography with a specific monoclonal antibody (Brown, et al., 1982, Nature, London 296:171–173). A nucleotide sequence coding for part of the determined amino acid sequence is then synthesized which can be used as a primer and/or probe. Parts of the amino acid sequence containing amino acid residues coded by a single codon or two codons are most suitable for this purpose. One approach is to synthesize a longer sequence, typically 25 to 60 nucleotides, which represents the most probable coding sequence based upon the known codon usage frequencies in humans. The use of two synthetic oligonucleotides based on different parts of the amino acid sequence facilitates the screening by allowing he to identify spurious positive hybridization signals. Additionally, the use of hybridization conditions that minimize the effect of GC-content on the melting point of DNA hybrids also facilitates the screening. Once a partial cDNA clone has been obtained by this method it may be used as a probe to help obtain a full-length cDNA clone.

(c) cDNA EXPRESSION LIBRARIES

Cloning vectors have been developed that allow for expression of the cDNA insert in bacteria. One approach, therefore, which can be used to obtain cDNA clones for tumor-associated proteins such as p97, is to prepare a cDNA library by reverse transcribing the mRNA (enriched or unenriched) isolated from melanoma cells as described above, using oligo(T)-nucleotide primers or the synthetic oligonucleotide primers described above, and to screen such a library with a monoclonal antibody directed against the melanoma associated p97 protein. Clones that contain DNA coding for the epitopes recognized by the monoclonal antibody in the correct orientation and reading frame will express peptides or proteins related to the melanoma associated p97 protein and can be identified by transferring the proteins expressed by the clones to a nitrocellulose filter and incubating the filter with the antibody, followed by development with a labeled anti-immunoglobulin reagent.

A potential problem is that many monoclonal antibodies fail to recognize the protein expressed by the bacteria because, in many cases, only a part of the cDNA will be contained in the insert and bacteria do not process proteins in the manner in which eucaryotic cells do. This problem is particularly acute for tumor cell surface proteins, which are modified more extensively by removal of the signal peptides, addition of carbohydrate side chains, and formation of disulfide bridges. It may therefore be necessary to generate monoclonal antibodies that are known to recognize the denatured antigen or to prepare polyspecific antisera by immunization with purified antigen.

Once a recombinant virus or plasmid that is believed to contain a cDNA insert derived from a melanoma associated p97 antigen is identified, the cDNA insert can be used to screen additional libraries in order to identify either full-length clones or else a group of clones that span the full length of the cDNA that codes of p97. The identity of the cDNA cloned can be established by sequence analysis and comparison of the deduced N-terminal amino acid sequence with that determined by direct amino acid sequence analysis of the p97 protein.

(d) GENOMIC CLONING

The following method allows cloning of DNA using a monoclonal antibody directed against an antigenic determinant that is present only in the native protein and is not present in nascent chains or in protein expressed in bacteria. To this end DNA derived from the human melanoma cell is introduced in mouse L cells by transfection. Subsequently, mouse cells that express melanoma associated p97 antigen are isolated either by using the fluorescence-activated cell sorter or by the immunological identification of colonies that produce p97 related peptides using radiolabeled monoclonal antibodies directed against p97 to detect related peptides on replicas of colonies transferred to polyester cloth filters. Several subsequent rounds of transfection may be required to remove unrelated human DNA sequences. A genomic library is then prepared in a lambda phage vector and screened for clones containing human repetitive sequences which occur in the introns of most genes. Once a genomic clone is identified it can be used as a hybridization probe to identify cDNA clones containing the DNA coding for p97.

5.2. Synthesis of Antigenic Fragments of the Melanoma-Associated p97 Antigen and Evaluation of Immunogenicity Synthetic peptides can be used as immunogens to elicit an immune response against the native protein than can provide a degree of protection against a number of pathogens. Such peptide sequences are selected from the known amino acid sequence of the protein antigen by identifying stretches of amino acids that are likely to be present on the surface of the protein molecule, exposed to the external medium. This is most commonly achieved by computer analysis of the amino acid sequence using established hydropathy parameters for the amino acids. Additional criteria such as the predicted secondary structure or flexibility may also be used.

Accordingly, synthetic peptides comprising 5 to 50 amino acid residues of the melanoma associated p97 protein may be tested for immunogenicity in experimental animals (usually mice of rabbits). Such synthetic peptides include but are not limited to all or part of the amino acid sequence substantially as depicted in FIG. 3 including: altered sequences in which functionally equivalent amino acid residues are substituted for residues within the sequence resulting in a silent change and/or modified or processed sequences such as glycosylated sequences, phosphorylated sequences etc., or chemically modified sequences. These p97 related peptides are used either alone or coupled to a carrier protein, such as keyhole limpet hemocyanin (KLH). In either case use of an adjuvant is optional, though preferable. The immunized animals are boosted and tested for antibodies directed against the immunized peptide. Those with anti-peptide antibodies are tested for antibodies that bind the native p97 protein. In the case of tumor-associated antigens such as p97 it is also of interest to test for a cellular immune response, for example, by looking for delayed-type hypersensitivity (DTH), for an antigen stimulated proliferation in vitro, for cytolytic T-cells, or for tumor rejection in an appropriate model. An appropriate model would be a mouse tumor expressing the human tumor-associated antigen as result of transfection with an appropriate cDNA expression vector construct.

The goal is to identify peptides that elicit a vigorous immune response directed against the melanoma-associated p97 antigen. Once identified, these peptides may be produced in large quantities by chemical synthetic methods known in the art. Alternatively, the identified peptides may be produced in large quantities by expressing the nucleotide sequences that code for such peptides in expression vector-host cell systems.

5.3. Production of p97-Related Peptides by Expression Vector-Host Systems

Proteins and peptides can be produced in large amounts by inserting nucleotide coding sequences into an appropriate expression vector, which is in turn introduced into suitable host cells, including, but not restricted to, bacteria, yeast, insect cells, and mammalian cells. Although bacterial hosts have many advantages, they do not process many eukaryotic proteins appropriately, and they are less suitable than eukaryotic cells for the expression of tumor-associated proteins. However, recombinant proteins produce in bacteria may be useful for induction of T-cell responses, since such responses are believed to require the initial degradation of the protein antigen.

In order to express p97 related peptides in a vector-host system, nucleotide sequences coding for the melanoma associated p97 antigen or a portion thereof, are inserted into an appropriate expression vector. Such nucleotide sequences include out are not limited to all or part of the DNA sequence of p97 substantially as depicted in FIG. 3 including altered sequences in which one or more codons within the sequence is substituted by a codon which encodes the same or a functionally equivalent amino acid residue, thus, resulting in a neutral or silent change in the sequence. The expression vector contains the necessary elements for the transcription and translation of the inserted protein-coding sequence. These elements vary in their strength and specificities. Depending on the host-vector system utilized, any one of a number of suitable transcription and translation elements may be used. For instance, when cloning in mammalian cell systems, promoters isolated from the genome of mammalian cells (e.g. mouse metallothionein promoter) or from viruses that grow in these cells (e.g. vaccinia virus 7.5K promoter) a may be used. Promoters produced by recombinant DNA or synthetic techniques may also be used to provide for transcription of the inserted sequences.

Specific initiation signals are also required for efficient translation of inserted protein coding sequences. These signals include the ATG initiation codon and adjacent sequences. In cases where either the gene or cDNA sequence is inserted into an appropriate expression vector, no additional translational control signals may be needed. However, in cases where only a portion of the coding sequence is inserted, exogenous translational control signals, including the ATG codon may have to be provided. The initiation codon must furthermore be in phase with respect to the reading frame of the protein coding sequences to ensure translation of the entire insert. These exogenous translational control sequences and initiation codon may be of a variety of origins, Both natural and synthetic.

Any of the methods known to those skilled in the art for the insertion of DNA fragments into a vector may be used to construct expression vectors containing a chimeric gene consisting of appropriate transcriptional an translational control signals and the protein coding sequences. These methods may include those used in vitro recombinant DNA techniques, synthetic techniques and in vivo recombinations (generic recombination).

Expression vectors include, out are not limited to the following; vectors and their derivatives: vaccinia virus, adenoviruses, insect viruses, yeast vectors, bacteriophage vectors, and plasmid DNA vectors. The cloning and expression of genes in bacterial systems is well known in the art. For instance, when cloning in an *E. coli*, its bacteriophages or plasmid promoters such as the lac promoter, trp promoter, recA promoter, ribosomal RNA promoter, the $P_R$ and $P_L$ promoters of coliphage lambda and others including but not limited to lacuv5, trp-lacuv5 (tac) hybrid promoter, ompF, bla, lpp and the like may be used to direct high levels of transcription of adjacent DNA segment. However, due to the processing differences between prokaryotic an eukaryotic cells, it may be preferable to express the p97 relate peptides of the present invention in eukaryotic cells. The best established methods of expressing proteins in eukaryotic cells are (a) introduction of the gene into the cell together with a drug resistance gene followed by selection with drug, preferably obtaining amplification as with the dihydrofolate reductase-methotrexate system; (o) expression of cDNA in a plasmid vector, often based upon pBR322, using a strong eukaryotic promoter and other regulatory sequences; (c) expression of cDNA in a viral vector, often derived from SV40, again using strong promoters, in this case an SV40 promoter. Recombinant plastic vectors are often used to produce cell lines than produce the protein over a long period of time, whereas SV40 vectors are often used to obtain transient expression. Although mammalian cells have most often been used as hosts, insect cells, and in come cases yeast cells, may also be suitable. Some are described in more detail below.

In order to construct a recombinant vaccinia virus expressing the melanoma associated p97 antigen, the cDNA coding sequence can be ligated to the 7.5K promoter of vaccinia virus to form a chimeric gene. This chimeric gene is flanked by additional vaccinia viral sequence homologous to the viral thymidine kinase gene, which is carried on the plasmid DNA vector. The construction of the chimeric gene involves the use of both natural and synthetic control signals for transcription and translation of the tumor-associated antigen sequence. The chimeric gene is then introduced into vaccinia virus expression vectors through in vivo recombination between the homologous thymidine kinase region present on both the plasmid vector and the vaccinia virus genome. These recombinant viruses containing the chimeric gene are capable of directing the expression of p97 related peptides in an infected host and can be used as components of a vaccine.

In cases where an adenovirus is used as an expression vector, the DNA sequence of interest is ligated to an adenovirus transcription/translation control complex, e.g., the late promoter and tripartite leader sequences This chimeric gene is then inserted in the adenovirus genome by in vitro or in vivo recombination. Insertion in a non-essential region of the viral genome (e.g., region E1 or E3) will result in a recombinant virus that is viable and capable of expressing the p97 related peptide in infected hosts. Presently, there are two strains of adenovirus (types 4 and 7) approved and used as vaccines for military personnel. They are prime candidates for use as vectors to express the inserted DNA sequence.

An alternative expression system which could be used to express the p97 related peptides is an insect system. In one such system, *Autographa californica* nuclear polyhedrosis virus (AcNPV) is used as a vector to express foreign genes. The virus grows in *Spodoptera frugiperda* cells. The DNA sequence of interest can be cloned into non-essential regions (for example the polyhedrin gene) of the virus and are placed under control of an AcNPV promoter (for example the polyhedrin promoter). Successful insertion of the DNA sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed.

In addition, host cell strains may be chosen which modulate the expression of the inserted sequences, or modify and process the chimeric gene product in a specific fashion desired. Expression from certain promoters can be elevated in the presence of certain inducers (e.g. zinc an cadmium ions for metallothionein promoters). Therefore, expression of the genetically engineered protein may be controlled. This is important if the protein product of the cloned gene is lethal to the host cells. Furthermore, modifications (e.g., glycosylation, phosphorylation, etc.) and processing (e.g., cleavage) of protein products are important for the structure and function of the protein. Different host cells have characteristic and specific mechanisms for the post-translational processing and modification of proteins. Appropriate cell lines or host systems can be chosen to ensure the correct modification an processing of the foreign protein expressed.

In the particular embodiment described herein for p97, we ligate the p97 cDNA sequence into an expression plasmid vector derived from pBR322 which contains the metallothionein promoter. The entire coding sequence-of p97 including the signal peptide and the amorane anchor was inserted into the vector.

5.3.1. Identification of Recombinant Expression Vectors Capable of Replicating and Directing the Expression of the p97 DNA Sequences Expression vectors containing foreign gene inserts can be identified by three general approaches: (a) DNA-DNA hybridization, (b) presence or absence or marker gene functions, and (c) expression of inserted sequences. In the first approach, the presence of a foreign gene inserted in an expression vector can be detected by DNA-DNA hybridization using probes comprising sequences that are homologous to the foreign gene insert. In the second approach, the recombinant vector/host system can be identified and selected based upon the presence or absence of certain "marker" gene functions caused by the insertion of genes in the vector (e.g. thymidine kinase activity, resistance to antibiotics, transformation phenotype,etc.). For example, if the foreign gene is inserted within the marker gene sequence of the vector, recombinants containing the DNA insert can be identified by the absence of the marker gene function. In the third approach, recombinant expression vectors can be identified by assaying the foreign gene product expressed by the recombinant. Such assays can be based on the physical, immunological, or functional properties of the gene product.

For example, when constructing a recombinant vaccinia virus according to the present invention, the chimeric gene containing the p97 coding sequences is inserted into the thymidine kinase gene, thereby inactivating an endowing on the virus a TK$^-$ phenotype. Such recombinants are selected by their ability to grow in media containing 5-bromo-deoxyuricine a nucleoside analog that is lethal to TK$^+$ cells but not TK$^-$ cells. The recombinants are further specific for the tumor-associated protein. TK$^-$ recombinant virus can be isolate by plaque-purification and stocks are prepared from infected cultured cells. The recombinant virus can be tested for its ability to induce synthesis of the p97 related peptides. To this end, infected cells can be grown in the presence of radiolabeled amino acids; then lysates and subcellular fractions of the infected radiolabeled cells are tested by immunoprecipitation with antibodies directed against the native melanoma associated p97 antigen. The immunoprecipitated products are resolved by SDS-PAGE. Infected cells can also rested by immunofluorescence using monoclonal antibody.

Cells into which a plasmid vector has been introduced by transfection can readily be identified by FACS analysis or by binding assays of replicas of cell colonies on polyester cloth. The amount of p97-related peptide present can be determined by a quantitative radioimmunoassay, and its subcellular localization can be determined by cellular fractionation and by immunofluorescence microscopy. The structure of the p97 related peptide expressed can be determine by SDS-PAGE and by amino acid sequence analysis.

5.3.2. Purification of the p97-Related Peptide from Expression Vector-Host Systems Many tumor-associated antigens such as p97 are cell-surface glycoproteins and contain an N-terminal signal peptide and a C-terminal anchor peptide (Davis et al., 1985, J. Mol. Biol. 181: 111–121). When expressed in an appropriate vector it is expected that the protein will be translocated to the cell surface. To facilitate purification of the protein it may be preferable to delete the DNA sequence cooing for the membrane anchor region, so that the mature protein is released into the culture medium.

The p97 related peptide can be purified from that host cells by detergent lysis followed by affinity chromatography using monoclonal antibodies. If a truncated protein is to be purified from the culture medium it is preferable to use serum-free medium, and then to use affinity chromatography with monoclonal antibodies. It is important that the antigen can be eluted from the antibody adsorbent without either reducing its antigenicity or denaturing it. This may be achieved by raising or lowering the pH or by using a chaotrope. It may e necessary to select a monoclonal antibody that will release the antigen under relatively mild conditions. The affinity-purified antigen may be purified further by HPLC.

5.4. Immunological Characterization of p97-Related Peptides

The ability of the synthetic or recombinant antigen to elicit an antitumor response can be evaluated initially in experimental animals. This is achieved by constructing a model system in which the human melanoma-associated p97 protein is expressed in cells of the appropriate inbred strain of the experimental specie. Animals are then immunized with the p97-related peptide of the present invention by various protocols and then tested for the development of antibodies directed against the melanoma-associated p97 antigen, for cell-mediated immunity such as delayed-type hypersensitivity to the p97 antigen, and for their ability to reject a challenge of viable, syngeneic tumor cells expressing the p97 antigen. In addition, in vitro assays of cellular immunity can be done to measure proliferation of lymphocyte in response to the p97 related peptide an the ability of lymphocytes from immunized animals, or human melanoma patients, to kill tumor cells expressing the p97 antigen. Moreover, by immunizing mice with mouse p97, one is able to determine the extent to which it is possible to induce an immune response to an antigen that is present in trace amounts in normal tissues.

Non-human primates may be used to establish the safety of the p97-related peptides of he present invention. To this end the animal can be immunized using protocols that could ethically be applied to human cancer patients, and then tested as described above, except that the tumor transplantation experiments will not be feasible, as these require the use of inbred strains. The safety of the immunization procedure is determined by looking for the effect of the immunization on the general health o: the immunized animals (weight changes, fever, appetite, behavior, etc.) and looking for pathological changes on autopsy.

Finally the p97-related peptide of the present invention can be tested in human cancer patients. After initial phase I testing in advanced cancer patients, to establish lack of toxicity, cancer patients in remission but with a high probability of recurrence could be tested. Their immune response would be evaluated as described above for non-human primates, except that the effect of the treatment on established disease or on the frequency of recurrence will be examined. In the case of the melanoma antigen p97 benign nevi (moles), which express the antigen, will also be examined.

5.5. Formulation of a Vaccine

The purpose of this embodiment of the invention is to produce, by synthetic or recombinant DNA techniques, a synthetic peptide, a purified protein, or a recombinant virus that may be use as an immunogen and a vaccine to protect cancer patients at high risk of recurrence of their disease, to treat established disease, an ultimately to vaccinate high-risk individuals prophylactically. In fact, the synthetic or recombinant melanoma-associated p97 antigen may be used in combination with other immunogens to prepare multivalent vaccines for the prevention of melanoma and other cancers. Examples of various vaccine formulations are discussed below.

5.5.1. Viral Vaccine Formulations

When the p97-related peptide of the present invention is produced by a recombinant virus, either a live recombinant viral vaccine or an inactivate recombinant viral vaccine can be formulated. The choice depends upon the nature of the recombinant virus use to express the p97 related peptide. Where the recombinant virus is infectious to the host to be immunized but does not cause disease, a live vaccine is preferable because multiplication in the host leads to a prolonged stimulus of similar kind and magnitude to that occurring in natural subclinical infections and, therefore, confers substantial long-lasting immunity. The infectious recombinant virus, upon introduction into a host, can express the p97-related peptide from its chimeric gene and thereby stimulate an immune response. The live recombinant virus by itself may be use as a preventative vaccine against melanoma. Production of such recombinant virus to be used in these formulations may involve both in vitro (e.g. tissue culture cells) an in vivo (e.g. natural host animal such as cows) systems. Conventional methods for the preparation an formulation of smallpox vaccine may be adapted for the formulation of live recombinant virus vaccine.

Multivalent live virus vaccines can be prepared from a single or few infectious recombinant viruses that express a variety of antigens of different tumor or cancer cells. For example, a vaccinia virus (which can accommodate approximately 35 kilobases of foreign DNA) can be engineered to contain coding sequences for other epitopes; such a recombinant virus itself can be used as the immunogen in a multivalent vaccine. Alternatively, a mixture of vaccinia and/or other viruses, each capable of directing the expression of a different gene coding for different epitopes can be formulated in a multivalent vaccine.

Whether or not the recombinant virus is infectious to the host to be immunized, an inactivated vaccine formulation may be prepared. Inactivated vaccines are "dead" in the sense that their infectivity has been destroyed, usually by treatment with formaldehyde. Ideally, the infectivity of the virus is destroyed without affecting the capsid or envelope proteins which carry the immunogenicity of the virus. In order to prepare inactivated vaccines, large quantities of the recombinant virus must be grown in culture in order to provide the necessary quantity of relevant antigens. A mixture of inactivated viruses which express different epitopes may be used for the formulation of "mulitvalent" vaccines. In some instances this may be preferable to live vaccine formulations because of potential difficulties with mutual interference of live viruses administered together. In either case, the inactivate recombinant virus or mixture of viruses should De formulated with a suitable adjuvant in order to enhance the immunological response to their antigens. Suitable adjuvants include, but are not limited to, mineral gels, e.g. aluminum hydroxide; surface active substances such as lysolecithin; pluronic polyols; polyanions; peptides; and oil emulsions.

Many methods may be used to introduce the vaccine formulations described above; these include but are not limited to: intradermal, intramuscular, intraperitoneal, intravenous, subcutaneous and intranasal routes. When a live recombinant virus vaccine formulation is used, it may be introduced via the natural route of infection of the parent wild type virus which was use to make the recombinant virus in the vaccine formulation.

5.5.2. Subunit Vaccine Formulations

In an alternative to viral vaccines, the p97-related peptide itself may be used as an immunogen in subunit vaccine formulations. Subunit vaccines comprise solely the relevant immunogenic material necessary to immunize a host. Accordingly, the p97-related peptide may be purified from recombinants that express the peptide. Such recombinants include any of the previously described virus-infected cultured cells, bacterial transformants, or yeast transformants. In another embodiment f the present invention, the p97-related peptides or proteins may be chemically synthesized.

Whether the p97-related peptides are purified from Q recombinants or chemically synthesized, the final product may be adjusted to an appropriate concentration and formulated with any suitable vaccine adjuvant and packaged for use. Suitable adjuvants include, but are not limited to: Mineral gels, e.g., aluminum hydroxide; surface active substances such as lysolecithin; pluronic polyols; polyanions; peptides; and oil emulsions. The p97-related peptide may also be incorporated into liposomes, or conjugated to polysaccharides and/or other polymers or use in a vaccine formulation.

In instances where the p97-related peptide is a hapten, i.e., a molecule that is antigenic in that it can react selectively with cognate antibodies, but not immunogenic in that it cannot elicit an immune response, the hapten may be covalently bound to a carrier or immunogenic molecule an the hapten-carrier may be formulates for use as a vaccine; for instance, a large protein such as protein serum albumin will confer immunogenicity to the hapten coupled to it.

6. EXAMPLE: MELANOMA ASSOCIATED p97 ANTIGEN

In the example described below, cDNA clones derived from various regions of p97 mRNA were pieced together and inserted into an expression vector which directs the expression of a peptide relate to p97. The p97-related peptides produced by the expression vector-host cell may be formulated in a vaccine.

6.1. Purification of p97 mRNA

Polysomes were prepared from SK-MEL28 melanoma cells (Carey et al., 1976, Proc. Natl. Acad. Sci. U.S.A. 73:3270-3282) by magnesium precipitation. From this preparation polysomes bearing p97 nascent chains were purified by incubation with 3 IgG2a monoclonal antibodies (96.5, 118.1, 133.2) specific for distinct epitopes of p97 (Brown et al., 1980, J. Biol. Chem. 255:4980-4983; Brown et al., 1981, J. Immunol. 127:539-546; Brown et al., 1981, Proc. Natl. Acad. Sci. U.S.A. 78:539-543; Plowman et al., 1983, Nature, London 303:70-72) followed by affinity chromatography On protein A sepharose. The p97-enriched mRNA was eluted using EDTA and purified by affinity chromatography on oligo(T)-cellulose (Bethesda Research Labs, Bethesda Md.). In a typical experiment, 150 $E_{260}$ units of polysomes yielded 260 ng p97-enriched mRNA, which represents 0.23% of the total mRNA. When translated in *Xenopus oocytes* and assayed for p97 as described (Brown et al. 1981, Proc. Natl. Acad. Sci. U.S.A. 78:539-543; Plowman et al., 1983, Nature, London 303:70-72), p97-enriched mRNA yielded 80 pg p97 per : mRNA, whereas p97-unenriched mRNA yielded only 0.44 pg p97 per : mRNA, showing that p97 mRNA activity had been enriched 180-fold. The yield of p97 mRNA activity was 42%. Translation in the reticulocyte lysate system (Pelham & Jackson, 1976, Eur. J. Biochem. 67:247-256) showed that p97-enriched mRNA coded for a major polypeptide with an apparent molecular weight of 84,000 daltons as analyzed by SDS-PAGE which was not detectable in the translation products of unenriched mRNA, and was immunoprecipitated by antiserum specific for p97 (FIG. 1). W concluded that this was the unglycosylated precursor of p97.

6.2. Preparation and Construction of cDNA Clones

Two techniques described below were used to construct cDNA clones transcribed from the mRNA templates isolate above.

6.2.1. Construction of cDNA Clones Primed by Oligo(T)

The p97-enriched mRNA prepared above was used as template for oligo(T)-primed cDNA synthesis. The cDNA was cloned in pBR322 as follows: for first strand cDNA synthesis, p97-enriched mRNA, the four dNTPs and oligo(T) (Collaborative Research, Walthma, Mass.) were incubated with reverse transcriptase (Molecular Genetic Resources). The second strand was synthesized by incubation with the large fragment of *E. coli* DNA polymerase (Bethesda Research Labs, Bethesda Md.), and the double stranded cDNA was digested with S1 nuclease (gift from D. Durnam of The Fred Hutchinson Cancer Research Center, Seattle, Wash.). The cDNA was then dC-tailed with terminal deoxynucleotidyl transferase (Bethesda Research Labs, Bethesda, Md.), annealed with PstI-digested, dG-tailed pBR322 (Bethesda Research Labs, Bethesda, Md.) (Villa-Komaroff et al., 1978, Proc. Natl. Acad. Sci. U.S.A. 75:3727-3731) and used to transform CaCl$_2$-treated *E. coli* RR1. DNA from colonies of transformed bacteria was bound to paper (Taub & Thompson, 1982, Anal. Biochem. 126:222-230) and screened by differential hybridization with cDNA probes synthesized on p97-enriched and unenriched mRNA templates.

A 243-base pair (op) clone, p97-3a2fl, was identified, which hybridized to p97-enriched cDNA bu not delectably to unenriched cDNA and also selected p97 mRNA in hybrid-selected translation experiments. A polyadenylation signal (AATAA) and a poly(A) tract were present at the 3' end of the cDNA (see FIG. 2). Nick translated p97-3a2fl hybridized 100-fold more strongly to p97-enriched mRNA than to unenriched melanoma mRNA, and not detectably to fibroblast mRNA. Northern blot analysis with the cloned cDNA as a probe identified an mRNA of approximately 4 kilobases (kb), which was present in SK-MEL 28 melanoma cells and absent from fibroblasts.

6.2.2. Genomic Cloning of p97 and the Use of Synthetic Oligonucleotides to Prime cDNA Synthesis Attempts to obtain cDNA clones extending more than 1 kb from the polyadenylation site were unsuccessful, possibly due to a region of high GC content (greater than 80%) with extensive secondary structure. Genomic cloning was used to circumvent this problem. Four overlapping genomic clones were isolated from libraries of lambda L47.1 containing size-fractionated SK-MEL 28 DNA enriched for a specific p97 restriction fragment. These four genomic clones span 28kb and contain the entire coding region of p97 including the regulatory region of the gene. The genomic as arranged sequentially from 5' to 3' are: lambda B15, lambda H17, lambda B6.6, and lambda E7.7. The nomenclature consists of a letter which refers to the restriction enzyme used to generate the fragment and the numeral indicating the kilobase size of the fragment which was cloned into lambda L47.1. Thus, starting from the 5' terminus, lambda clone B15 contains a 15kb BamHI p97 fragment; lambda clone H17 contains a 17kb HI:ndIII p97 fragment; lambda clone B6.6 contains a 6.6kb BamHI p97 fragment; and lambda clone E7.7 contains a 7.7kb EcoRI p97 fragment (see FIG. 2A). Restriction fragments of the clones that hybridized to the 4 kb p97 mRNA on Northern blots were sequenced and p97 exons were identified by a computer assisted homology search between the predicted coding sequences and the amino acid sequence of human and chicken transferrin (Yang et al., 1984, Proc. Natl. Acad. Sci. U.S.A. 81:2752-2756; McGillivray et al., 1982, Proc. Natl Acad. Sci. U.S.A. 79:2504-2508; Jetsch & Chambon, 1982, Eur. J. Biochem. 122:291-295).

Three synthetic oligonucleotides, the sequences of which were based on p97 genomic exon sequences, were used to prime cDNA synthesis on SK-MEL 28 mRNA and the resulting cDNA was cloned into lambda-gt10 as follows: the p97 cDNA was detailed and ligated with a bridger oligonucleotide (AATTCCCCCCCCCCCC) and lambda-gt10 which had been restricted with EcoRI. The bridger oligonucleotide permitted insertion and ligation of the detailed cDNA sequence into the EcoRI site of lambda gt10. The lambda phage was packaged (Grosveld et al., 1981, Gene 13:227-237), and plated on *E. coli* $c_{600}$ rK$^-$mK$^+$hfl. The cDNA libraries in lambda-gt10 were screened for the p97 insert by plaque hybridization (Benton & Davis, 1977, Science 196:180) with genomic exon fragments as probes. Probes were radiolabeled with 32P-TTP (New England Nuclear, 3200 Ci/mmole) by nick-translation to a specific activity of $5-10 \times 10^8$ cpm/$\mu$g. Three overlapping cDNA clones (10al, 1jl, 2fl) spanning 2,368 nucleotides of the p97 mRNA, including the entire coding region, were identified by using p97 exon specific fragments as probes (FIG. 2).

6.3. DNA Sequence Analysis of p97 cDNA inserts were excised and subcloned into plasmid vector pEMBL18+ (Dente et al., 1983, Nucleic Acids Res. 11:1645-1655) in *E. Coli* for subsequent propagation and restriction mapping. cDNA was also subcloned into M13mp18 phage cloning vector (Yanish-Perrone et al., 1985, Gene 33:103-119) and sequenced using the dideoxy method of Sanger (Sanger et al., 1977, Proc. Natl. Acad. Sci. U.S.A. 74:5463-5467). M13 clones containing large inserts were sequenced by generating deletions using DNAse I (Hong, 1982, J. Mol. Biol. 158:539–549) or exonuclease III (Henikoff, 1984, Gene 28 351–359), and by using synthetic 21-mer oligonucleotide primers.

The p97 cDNA sequence is shown in FIG. 3. An open reading frame of 2,214 nucleotides extends from the first ATG, the sequence around which conforms with the consensus initiation sequence determined by Kozak (Kozak, 1980. Nucleic Acids Res. 8:127–142), to the TGA at position 2,215. The most 5' cDNA clone contains an additional 60 nucleotides upstream of the initiating ATG. The 3' non-coding region of p97 mRNA, which was not obtained as a cDNA clone, was identified as a single genomic exon containing 1,667 nucleotides. Residues 20–32 of the predicted amino acid sequence are identical to the known N-terminal amino acid sequence of p97 (Brown et al., 1982, Nature, London 296:171–173), proving the identity of the cloned cDNA. Furthermore, the predicted molecular weight of the precursor is 80,196 daltons, in good agreement with the observed molecular weight of the in vitro translation product.

6.4. Construction of a Recombinant Expression Plasmid Containing the p97 Coding Sequence The large size of the p97 gene necessitated piecing together the cDNA clones that were obtained by specific priming of melanoma mRNA with reverse transcriptase. The three cDNA lambda gt10 clones (10al, 1jl, and 2fl; see FIG. 2) that encompassed the coding region from the signal peptide through the membrane anchor sequence were used. The p97 insert of clone 10al was excised by digestion with EcoRI and the oligo(dG) sequence at the 5' end of the cDNA 10al was removed by digestion with exonuclease III, generating clone 10alb, with a HindIII site 30 bp upstream from the initiating methionine of the p97 preprotein. The p97 inserts of the three cDNA clones 10alb, 1jl, and 2fl, and genomic clone E7.7 were ligated together at PvuII, SstI and EcoRI restriction enzyme sites and inserted into the HindIII-EcoRI sites of the plasmid vector pEMBL18+ (Dente, et al. 1983, Nucl. Acids Res. 11:1645–1655) as shown in FIG. 2. The final construct, p97b, contains the 4.4 kb p97 insert in plasmid vector pEMBL18+ which was used to transform E. coli HB101. The insert in p97b contains 30 bp of the 5' untranslated region of p97 mRNA, the entire coding sequence, and the 3' untranslated region, bounded by a 5' HindIII site and a 3' EcoRI site.

The 4.4 kilobase p97 insert was excised from p97b with HindIII and EcoRI, and the ends were filled in using the Klenow fragment of E. coli DNA polymerase. The blunt-ended fragment was inserted into the unique SmaI site in the eukaryoric cDNA expression vector 1995.12 pUC13, a derivative of vector mThGH-112, (Palmiter et al., 1983, Science 22:809–14), which was obtained from Dr. Richard Palmiter (University of Washington, Seattle, Washington). This vector uses the mouse metallothionein promoter to express foreign genes in eukaryotic cells. The construct with the p97 insert in the correct orientation was identified by restriction analysis and designated pMTp97b.

The recombinant plastic was transfected into LMTK⁻ cells, and transfectants were selected by growth in HAT medium. Clones picked from the transfected dish were expanded in 96-well microtest plates, and spent culture medium and cell lysates from replicate plates were assayed for p97 by a two-site immunoraciometric assay. Subclones were expanded and retested. Clone.TKMp97-12 which expresses approximately 4,000,000 molecules of p97 per cell was grown up, induced with cadmium, and used as a source of p97 for immunization.

6.5. Immunization of Mice with p97 Related Peptides

The TKMp97-12 cells were grown up, induced with cadmium and (14.4 g) were lysed by incubation for 10 minutes on ice with 70 ml TNEN (20 mM Tris-HCl, pH 8.0, 100 mM NaCl, 1 mM EDTA, 0.5% NP-40). The lysate was ultracentrifuged at 200,000×g for 45 minutes at 4° C., an half of the lysate was passed over a 1 ml immunoaffinity column specific for p97 (Fab fragment of antibody 96.5 coupled to Sepharose). The immunoadsorbent was washed extensively, first with TNEN, and finally with 20 mM Tris-HCl, pH 6.8.

For the immunization, 0.5 ml of the adsorbed immunoaffinity column prepared as described above was mixed with 0.5 ml 20 mM Tris-HCl, pH 6.8, and emulsified with 1 ml complete Freund's adjuvant. Four BALB/c mice each received 0.4 ml of the emulsion intraperitoneally. Three weeks later the mice were boosted with one fourth of this amount of antigen in incomplete Freund's adjuvant. Control mice were immunized with an immunoaffinity column of an antibody unrelated to p97 that had been otherwise treated identically. Four of the p97-immunized mice an two control ice were bled one week after the boost. The sera were tested for antibodies to p97 by immunoprecipitation from radioiodinated SK-MEL melanoma cells followed by SDS-PAGE. The results showed that sera from the four p97-immunized mice immunoprecipitated p97, whereas the control sera were negative. The sera were also tested for the presence of antibodies directed against p97 using an ELISA assay on glutaraldehyde-fixed SK-MEL 28 melanoma cells (20,000 cells per microtest well). The fixed cells were incubated with 0.05 ml serum diluted 1/10,000 for 1 hour at room temperature, washed, and then incubated for 1 hour at room temperature with 0.05 ml horseradish peroxidase-conjugated goat anti-mouse IgG (Southern Biotech). The optical densities (read at 490 nm) of sera from the p97-immunized mice were 0.350, 0.243, 0.343, 0.200, whereas the optical density of sera from controls were 0.036 and 0.057.

6.6. Characterization of p97

6.6.1. Structure of p97

The structure of p97 was determined from the amino acid sequence of the p97 precursor which comprises four structural domains. Since residue 20 of the precursor sequence corresponds to the N-terminus of mature p97, amino acid residues 1–19 probably contribute a signal peptide, a conclusion that is supporter by its length and hydrophobic nature. Amino acids 20–361 and 362–713 comprise two homologous obtains of 342 and 352 amino acids. Potential N-linked glycosylation sites occur at positions 38 an 135 in the N-terminal domain and position 515 in the C-terminal domain. Finally, we believe that amino acids 714–738, a region of predominately uncharged and hydrophobic residues, anchor p97 in the cell membrane (Davis et al., 1985, J. Mol. Biol. 181:111–121) and may extend into the cytoplasm.

The domain structure of p97 is supported by the protease digestion experiments. Digestion of p97 with trypsin, papain (Brown et al., 1981, J. Immunol. 127:539-546) or thrombin produced a glycosylated, antigenic fragment of approximately 40,000 daltons in molecular weight. The fragment was purified from a thrombin digest of p97 that has been metabolically labelled with $^{35}$S-methionine or $^{35}$S-cysteine and sequenced as described (Brown et al., 1982, Nature, London 296:171-173). Cysteine residues were identified at positions 7 and 17, and methionine residues at positions 2 and 20. Identical results were obtained with intact p97, and are in complete agreement with the N-terminal sequence of p97 predicted from the cDNA sequence. We conclude that the 40,000 dalton molecular weight protease-resistant fragment corresponds to the N-retinal domain of p97. We have been unable to isolate the C-terminal domain of p97, possibly because it is protease-sensitive.

6.6.2. Homology of p97 with Transferrin

A search of the amino acid sequence library of the Protein Identification Resource (Release 5.0; Dayhoff et al., 1981, Nature, London 290:8) showed that p97 is strikingly homologous to three members of the transferrin superfamily: human serum transferrin, human lactotransferrin an chicken transferrin (37%-39% homology, see FIG. 4). Since human and chicken transferrin show 50% homology to each other, p97 must have diverged from serum transferrin more than 300 million years ago. p97 has 14 cysteine residues located in homologous positions in each domain. Human transferrin contains all of these cysteines in homologous positions in both domains, while human lactrotransferrin and chicken transferrin lack only two of these cysteine residues (in their C-terminal domains). Unlike p97, these proteins contain 4-7 additional cysteines in their C-terminal mains which have no corresponding member in the N-terminal domain. Human transferrin also contains 2 extra cysteines unique to its N-terminal domain. The positions t st of the disulfides in human serum transferrin, lactotransferrin and chicken transferrin have been determined directly (McGillivray et al., 1982, Proc. Natl. Acad. Sci. U.S.A. 79:2504-2508; Metz-Boutigue et al., 1984, Eur. J. Biochem 145:659-676; Mazurier et al., 1983, Experietia (Basel) 39:135-141; MacGillivray er al., 1983, J. Biol. Chem. 258:3543-3553; Williams et al., 1982, Eur. J. Biochem. 122:297-303; Williams, 1974, Biochem J. 141:745-752). One can thus predict the presence of 7 disulfide bonds in each domain of p97 (see FIG. 5).

The amino acid homology between domains of p97 (46%—achieved by insertion of 7 gaps of 9 residues) is more 25 striking than that seen in human transferrin (43%—16 gaps, 45 residues) or chicken transferrin ($^{35}$%—12 gaps, 49 residues). Given the extensive sequence homology between p97 and transferrin, and the apparently similar folding patterns, based upon the conservation of cysteines, we believe that if the present low-resolution X-ray structure of transferrin (Gorinsky et al., 1979, Nature, London 281:157-158) can be refined it may be possible to deduce the three-dimensional structure of p97.

6.6.3. Function of p97

Its membership in the transferrin superfamily, its ability to bind iron (Brown et al., 1982, Nature London 296:171-173), and its common chromosomal localization with transferrin and the transferrin receptor (Plowman et al., 1983, Nature, London, 303:70-72; Yang et al., 1984, Proc. Natl. Acad. Sci. U.S.A. 81:2752-2756) all support a role of p97 in iron transport. The iron binding pocket of transferrin is thought to contain 2-3 tyrosines, 1-2 histidines and a single bicarbonate-binding arginine (Metz-Boutigue et al., 1984, Eur. J. Biochem. 145:659-676). Conservation of these amino acids in p97 support its proposed role in iron metabolism (see FIG. 4). Since p97 is a membrane bound transferrin-like molecule and has no homology with the transferrin receptor (Schneider et al., 1984, Nature, London, 311:675-678), its role in cellular iron metabolism may differ from that provided by circulating serum transferrin and the cellular receptor for transferrin. Expression of the cloned p97 cDNA in eukaryotic cells will allow experimental testing of its functional properties.

6.6.4 Conclusion

Based on these data it is clear that cDNA constructs for the melanoma-associated p97 have been obtained and that these can be expressed efficiently in mammalian cells to produce large amounts of antigenic p97.

7. EXPRESSION OF CLONED p97 AND VACCINE TESTING

The experiments detailed herein describe the expression of the cloned p97 protein and its vaccine testing. Expression of p97 protein in a secreted form (by the transfected mouse cell clone B16svp97a.14) enabled purification of milligram quantities of the full length p97 protein. The protein in purified form was used for in vitro testing of induction of cellular immunity and for testing its potential as a subunit vaccine. The p97 gene product was also expressed on the cell surface of metastatic murine melanoma cells, providing a model for testing the efficacy of vaccines in preventing tumor growth in a syngeneic system.

The p97 gene was inserted into a live vaccinia recombinant virus for use as a vaccine formulation capable of generating effective cellular immunity. The recombinant vaccinia virus, Vp97a-NY, was evaluated for its ability to generate immunity in mice, using a variety of assays for demonstrating humoral and cellular immunity. Using the syngeneic murine tumor model described supra, the Vp97a-NY recombinant virus vaccine was demonstrated to provide a protective effect from tumor cell challenge. The vaccine also provided a therapeutic effect in mice with existing growing lung metastases, a property which is analogous to the proposed use of the vaccine for generating an immunotherapeutic anti-tumor response in human melanoma patients with existing tumor.

In addition to the mouse studies, where there is only 91% homology between human p97 and the mouse homologous protein (over the regions examined thus far), the Vp97a-NY vaccine has also been tested in non-human primates. There is a much closer homology between human p97 and the monkey form of the protein (as revealed by the cross-reactivity at the monoclonal antibody level). Because of the potential difficulty in generating an immune response against a "self" protein, the closely related Macaque monkey was used to test the immunogenicity of the Vp97a-NY vaccine. The recombinant vaccinia vaccine was tested in monkeys and shown to induce humoral immunity directed against the p97 protein. Thus far the monkeys have exhibited no noticeable symptoms of deleterious side effects from exposure to the vaccine, after having received two inoculations of the live recombinant vaccinia virus, over a period of six weeks.

7.1. Plasmid Expression

The expression plasmid driven by the SV-40 early promoter sv2 was constructed from the cDNA plasmid clone p97a, which is similar to plasmid p97b, except that the entire 3'UT region is utilized (FIG. 6). All cDNA clones were originally isolated from lambda gt10 libraries with synthetic EcoRI-dG (9-17) linkers as previously described. Inserts were excised by EcoRI and subcloned into pEMBL18+ for subsequent propagation and characterization. Clone 10al was subcloned into M13mp18 and an RF form was digested with BamHI and SphI, treated briefly with Exonuclease III, blunted with S1 nuclease, treated with Klenow, and religated. Several plaques were isolated and sequenced, one of which had removed the dG tail and retained 33 bp of the p97 5' untranslated region inserted into the HindIII site of M13mp18. An RF of this subclone (10ala) was used for generating the intact p97 cDNA; otherwise, all fragments were isolated from the plasmid subclones. The 550 bp HindIII-PvuII fragment from 10ala and the 735 bp PvuII-SalI fragment from 1jl were isolated from LMP agarose gels and ligated into pEMBL18+ at the SalI and HindIII sites, generating p5'p97. E7.7 genomic clone in pEMBL18+ was digested to completion with EcoRI and digested partially with SstI, and the 4.5 kb fragment was separated by fractionation through 0.8% LMP agarose. This 4.5 kb 3' fragment was ligated with the 404 bp SstI fragment from 2fl and the 535 bp BamHI-SstI fragment from 1jl into pEMBL18+ at the SalI and EcoRI sites, generating p3'p97. The 1285 bp HindIII-SalI fragment of p5'p97 was then ligated into p3'p97, generating pp97a. The EcoRI-partial HindIII fragment from this clone was inserted into pSV2neo (Southern, et al., 1982, J. Mol. App. Genet. 1:327-341) at the HindIII and EcoRI sites, eliminating the neomycin coding region and SV40 splice/polyA sequences while retaining the SV40 early promoter and 72 bp enhancer, 33 bp p97 5'UTR, the entire p97 coding region, 3' UTR and 1.4 kb 3' flanking DNA. The resulting plasmid was termed pSVp97a.

The sv2 driven plasmid was transfected by calcium phosphate precipitation into a variety of eukaryotic cell lines, and expressing cells were cloned and selected using co-transfection of a dominant selectable marker. To accomplish this, Chinese hamster ovary (CHO) cells were cultured in Hank's F1 medium containing 15% fetal calf serum (FCS), 4mM L-glutamine, 1.3 mM proline, and antibiotics. B16 cells were cultured in RPMI medium containing 0.15% bicarbonate and 1735 cells in DMEM medium (Gibco) both supplemented with 15% FCS, and antibiotics. Cells were transfected by a modified calcium phosphate technique (Wigler M., et al., 1978, Cell 14:725-731) with 20 ug per plate of pSV2p97a plasmid DNA and 0.5 ug of either pSV2DHFR or pSV2neo respectively. All plasmids were linearized at the EcoRI site. Stable tranfectants were selected using hypoxanthine negative (HAT−) medium for CHO cells or 0.5 ug/ml Geneticin (G418, Gibco) for the B16 and 1735 cells. Surviving cells began forming visible colonies 7 days after transfection and were overlaid with sterile polyester filters held in place by glass beads. The filters remained in place for five days, allowing the cells to grow up into the polyester matrix, generating a replica of the colonies on the plate. The filters were then removed and used for a live cell binding assay with iodinated anti-p97 monoclonal antibody. Ten micrograms of labeled monoclonal antibody were incubated with up to 20 filters in 10 ml FCS at 4° C. for one hour. The filters were washed extensively in phosphate-buffered saline (PBS), dried and exposed to XAR-5 film overnight at −70° C. Filters were subsequently stained with 7% methylene blue to visualize the cell colonies. In all the cell lines used except the B16 mouse line, the expressing cells contained antigenic p97 protein on their cell surfaces.

In the B16-transfected cells, p97 was released into the medium, a finding unique to this cell type. The secretion of p97 enabled purification of full length p97 protein from the medium of the cells. Clone B16SVp97a.14 expressed approximately 4 ug/ml of p97 in spent medium. Recombinant p97 was purified from spent medium of transfected clone B16SVp97a.14, which shed large quantities of p97 antigen into the medium. Cells were maintained at near confluency ($10^9$ cells) in 850 $cm^2$ roller bottles by continually adding small amounts of fresh medium. They continued to shed antigen without detaching for weeks, allowing continual harvest and freezing down of spent medium. The purification of p97 was accomplished by immunoaffinity chromatography, using sepharose linked to Fab fragments of monoclonal antibody 96.5. To this end, three liters of spent medium was run over a series of three 30 ml columns. The first contained 15 ml of G-25 superfine Sephadex (Pharmacia), the second contained 20 ml of Sepharose 4b (Pharmacia), and the third contained 8 ml of cyanogen bromide-activated Sepharose (Sigma) conjugated to Fab fragments of monoclonal antibody 96.5 (10 mg protein/ml of Sepharose). Subsequently, the affinity column was washed extensively with cold PBS and the antigen was eluted with 30 ml of 0.1 M citrate, pH 5 and 30 ml of 0.1M citrate, pH 4. These conditions were shown not to alter the immunoreactivity of the antigen, while accomplishing complete elution of the antigen from monoclonal antibody 96.5. The two elutions were neutralized with 3.0 ml and 4.5 ml, respectively, of 2 M Tris, pH 8. The purified eluate was concentrated using an Amicon apparatus with a PM10 filter, and washed with two 10 ml volumes of PBS, leaving a final yield of 4.95 mg in 4.5 ml as determined by Bradford assay (Biorad). Fifteen ug of the product was run on SDS-PAGE (FIG. 7) and visualized both by Coomassie Blue and silver stain. A double determinant immunoassay (DDIA) (Brown, et al. 1981, Proc. Natl. Acad. Sci. 78:539) provided an independent confirmation of the molar quantity of purified protein. Control preparations were performed in parallel with spent medium from the parental B16 cell line, and showed no detectable protein. In a subsequent preparation 30 mg of 95% pure p97 protein was purified from 300 mg of monoclonal antibody 96.5 Fab fragments conjugated to Sepharose. The purified p97 protein was immunogenic producing a strong antibody response in mice immunized with the protein as described in Section 7.3. infra.

7.2. Construction and Expression of Recombinant p97 Vaccinia Virus

The coding region of p97 was inserted by cutting p97a with HindIII, converting the ends to blunt ends, and ligating into the vaccinia insertion vector pGS-20 (Mackett et al., 1984, J. Virol. 49:857-864) which had been opened at the SmaI site. The PGS-20 vector utilizes the 7.5K promoter, and contains flanking sequences from the vaccinia thymidine kinase (TK) gene. A recombinant virus was generated by the method or Mackett et al., supra, and Vp97a-NY was isolated which causes infected cells to express p97 protein of the correct size and glycosylation (FIG. 8). Surface expression of p97 was also confirmed in cells infected with the recombinant p97 virus (Table I) below.

TABLE I
SURFACE p97 EXPRESSION OF TRANSFECTED MOUSE CELLS AND CELLS INFECTED WITH RECOMBINANT VACCINIA VIRUS[1]

| Cell Type | Virus Used to Infect Cell | Molecules of p97 Expressed per Cell |
|---|---|---|
| M2SVp97a.A | None | 3,210,000 |
| M2svp97a.E/F2 | None | 434,000 |
| M2 parent | None | 2,000— |
| BSC | None | 5,590 |
| BSC | Vwt-NY vaccinia | 5,220 |
| BSC | Vp97a-NY vaccinia | 1,140,000 |

[1]Cells were trypsinized briefly, washed and aliquoted into tubes containing $10^3$, to $10^4$ or $10^5$ cells. Non-expressing carrier cells were added to tubes with lower cell numbers so that a total of $10^5$ cells were used per tube. $1 \times 10^6$ cpm of iodinated monoclonal antibody 96.5 (123 ng) was incubated, in a total volume of 50 ul, with the cells for 60 minutes on ice. Cells were washed and spun 4 times in PBS + 10% fetal calf serum, then resuspended and counted in a Micromedic 4/600 plus gamma counter.
—signifies less than.

7.3. Recombinant p97 Vaccinia Virus is Immunogenic in Mice

Inoculation of mice with Vp97a-NY generated a strong humoral antibody response. Mice were immunized once, boosted once at four weeks, then bled at five weeks. Titers were assessed by ELISA, using antigen-coated plates and a Protein A conjugated to horseradish peroxidase as detection reagent. Data were converted to monoclonal antibody equivalents by comparison to a standard curve for ELISA binding generated using anti-p97 monoclonal antibody 133.2. The results showed a strong induction of serum antibody (FIG. 9). Cellular immunity was detected using an in vitro proliferation assay with purified p97 protein as the stimulating antigen (Table II).

TABLE II
PROLIFERATION ASSAY OF MURINE SPLEEN CELLS[1]

| Stimulating Antigen | Proliferative Index of vp97 Recombinant Immune Spleen Cells | Proliferative Index of Control Spleen Cells |
|---|---|---|
| Con A (10 ug/ml) | 71 | 50 |
| p97 Protein | | |
| (3 ug/ml) | 27 | 2 |
| (10 ug/ml) | 43 | 2 |
| (20 ug/ml) | 56 | 2 |
| (50 microgr/ml) | 44 | 3 |
| UV-Inactivated Vaccinia Virus (10 pfu/ml) | 91 | 2 |
| P97-Transfected Irradiated Syngeneic Tumor Cells ($10^4$) | 86 | 2 |
| Parental Irradiated Tumor Cells ($10^4$) | 3 | 1 |

[1]Spleen cells were isolated from mice inoculated by tail scarification with $10^7$ pfu Vp97a-NY recombinant virus, boosted one month later with the same dose and killed one week subsequently. Naive spleen cells were used for controls in this experiment. $10^5$ cells were cultured per well in 96-well round bottom plates in 0.22 ml RPMI supplemented with 0.5% normal mouse serum, penicillin/streptomycin, glutamine, bicarbonate, and $2.5 \times 10^5$ M 2-mercaptoethanol. Cultures were pulse-labeled for six hours on day four, with 25 uCi/well tritiated thymidine (New England Nuclear), harvested with a PHD cell harvester, and counted using Optifluor in a Beckman LS 3801 counter. Proliferation indices were calculated by dividing cpm averages of quadruplicate wells stimulated with each antigen by the average cpm average of control (media).

The results shown in Table II indicate that T cells are proliferating in response to the p97 protein antigen.

In order to ascertain whether helper cells were also stimulated by the recombinant virus in spleen cells from immunized mice, the cells were stimulated in vitro and the supernatants assayed for production of interleukin-2 (IL-2), a helper T cell factor. Spleen cells were cultured from mice immunized twice previously with recombinant Vp97a-NY vaccinia or parental vaccinia. 10 cells were incubated for 48 hours in 0.2 ml of medium identical to that used for proliferation assays, in 96-well round bottom plates, in the presence or absence of the stimulation antigen. Supernatants were collected, pooled from four wells, and frozen prior to IL-2 assay. The IL-2 assay utilized $10^4$ previously IL-2 starved mouse T cell line CTLL cells incubated in each well with varying dilutions of assay supernatant with Click's Medium, in triplicate. A standard curve was constructed with recombinant IL-2 obtained from Genentech, CA. CTLL cells were pulse-labeled with thymidine according to the usual proliferation assay technique in the last six hours of 24 hour incubation, then harvested and counted as described for the proliferation assay methods. The results shown in Table III indicate that IL-2 production from spleen cells of mice immunized with recombinant p97 vaccinia virus is stimulated in vitro by p97.

TABLE III
STIMULATION OF IL-2 PRODUCTION BY p97 IMMUNE SPLEEN CELLS

| Vaccination Immunogen | In vitro Stimulus | Units IL-2 Produced |
|---|---|---|
| Vp97a-NY | p97 Protein (20 ug/ml) | 4.4 |
| Vp97a-NY | Medium | 0.25 |
| Vwt-NY | p97 Protein (20 ug/ml) | 0.25 |
| Vwt-NY | Medium | 0.25 |

In addition, a delayed type hypersensitivity response was measured using the foot-pad swelling assay in Vp97a-NY inoculated mice. Five mice (C3H/Hen strain) per group were inoculated by tail scarification with recombinant or parental strain vaccinia virus. Six days later, the hind paws of each mouse were challenged by inoculation of 20 ul PBS or 20 ul cells in PBS ($5 \times 10^5$ cells per mouse). The foot pads were measured 24 hours later in a double blind manner, using a Fowler micrometer. The foot pad thickness of the PBS-injected foot pad was substracted from the measured thickness of the experimental foot from each mouse, and means as well as standard deviations of the incremental foot pad swelling were calculated. The results shown in Table IV show the induction of a p97-specific delayed type hypersensitivity response in mouse immunized with recombinant p97 vaccinia virus.

TABLE IV
ANTIGEN-SPECIFIC FOOTPAD SWELLING IN p97 IMMUNE MICE

| Vaccination Immunogen | Challenging Antigen | Footpad Swelling (mm $\times 10^{-2}$) |
|---|---|---|
| Vp97a-NY | p97-transfected syngeneic tumor cells | 40.3 (+/−6.8) |
| Vp97a-NY | parental syngeneic tumor cells | 3.0 (+/−2.8) |
| Vwt-NY | p97-transfected syngeneic tumor cells | 1.5 (+/−2.3) |
| Vwt-NY | parental syngeneic | 5.5 (+/−5.0) |

TABLE IV-continued

| Vaccination Immunogen | Challenging Antigen | Footpad Swelling (mm × 10⁻²) |
|---|---|---|
| | tumor cells | |

ANTIGEN-SPECIFIC FOOTPAD SWELLING IN p97 IMMUNE MICE

7.4. Protection and Therapy with p97 Vaccinia Virus in a Murine Tumor Model

In order to assess vaccination efficacy, mice were vaccinated with various protocols using the recombinant p97 vaccinia virus of the invention and then challenged with a p97-transfected syngeneic tumor cell (M2SVp97a.2E). To this end, mice were immunized with Vp97a-NY recombinant live vaccinia virus or the parental strain (Vwt-NY) by tail scarification; or with 100 ug purified p97 protein or $5 \times 10^6$ irradiated M2-K1735 tumor cells intraperitoneally in complete Freund's adjuvant. An intravenous tumor cell challenge was given two weeks following the last vaccination by injection of M2SVp97a.2E, a metastatic tumor clone prepared from M2-K1735 (a murine melanoma model) by transfection with the human p97 coding sequence contained in an expression plasmid driven by the SV40 early promoter. A variety of expressing clones were selected, and the one used for tumor challenge, clone M2SVp97a.2E, expresses a medium level of p97, about 400,000 molecules per cell or equivalent to human melanoma p97 antigen density. Two doses of intravenous tumor challenge were used, $5 \times 10^5$ or $1 \times 10^5$ cells which were injected into the tail vein of syngeneic C3H/Hen mice. The mice were sacrificed 16 days after tumor challenge and lungs were removed. A mouse was scored as positive if there were tumors visible to the naked eye on lungs stained with India ink. The results are shown in Table V.

TABLE V

CHALLENGE OF VACCINATED MICE WITH SYNGENEIC p97 TRANSFECTED MELANOMA CELLS

| Vaccine | No. of Immunizations | Challenge Cell Dose | No. of Mice with Obvious Lung Metastasis |
|---|---|---|---|
| Vp97a-NY | 2 | 5 × 10⁵ | 1/5 |
| Vp97a-NY | 1 | 5 × 10⁵ | 2/4 |
| Irradiated Syngeneic Melanoma Cells | 2 | 5 × 10⁵ | 0/4 |
| Vwt-NY | 2 | 5 × 10⁵ | 9/10 |
| p97 Protein | 2 | 5 × 10⁵ | 3/3 |
| Vp97a-NY | 2 | 1 × 10⁵ | 0/1 |
| Vp97a-NY | 1 | 1 × 10⁵ | 0/4 |
| Naive | 0 | 1 × 10⁵ | 5/6 |

The results presented in Table V demonstrate that there was a considerable protective effect with two immunizations of Vp97a-NY although no protective effect was seen with the purified p97 protein vaccine (despite the extremely high antibody titers elicited). The ability of the recombinant virus to elicit cellular immunity may be responsible for its protective tumor immunity.

In a therapy experiment, mice were inoculated with a low dose of p97-expressing tumor cells and then two days later, inoculated with the recombinant vaccinia vaccine. Mice were challenged with $10^5$ or $10^4$ p97-expressing tumor cells (M2SVp97a.E) intravenously. Two days later, mice were inoculated by tail scarification either with Vp97a-NY or Vwt-NY. Weekly inoculations by tail scarification were repeated, and mouse survival recorded the results shown in FIG. 10 indicate the therapeutic effect of recombinant p97 vaccinia virus vaccination in mice with existing lung metastasis.

7.5. Recombinant p97 Vaccinia Virus is Immunogenic in Macaque Monkeys

Two *Macaca fasicularis* (macaque) monkeys were scarified with either $2 \times 10^8$ plaque forming units (pfu) of Vp97a-NY recombinant vaccinia, or the same dose of parental strain vaccinia. Two weeks later the sera were tested by ELISA for titers to vaccinia and p97. The results shown in Table VI demonstrate that humoral antibodies to p97 were detectable two weeks after the single inoculation with Vp97a-NY.

TABLE VI

SERUM ANTIBODY TITERS IN VACCINIA INOCULATED MONKEYS

| Immunogen/Week | Anti-Vaccinia Titer (serum dilution with twice background) | Anti-p97 Titer (ug/ml monoclonal antibody equivalents) |
|---|---|---|
| Vp97a-NY/Week 0 | 1/20 | 0.54 |
| Vp97a-NY/Week 2 | 1/2000 | 6.54 |
| Vwt-NY/Week 0 | 1/20 | 0.50 |
| Vwt-NY/Week 2 | 1/2000 | 0.34 |

8. DEPOSIT OF MICROORGANISMS

The following *E. coli* strain carrying the listed plasmid has been deposited with the ATCC, Rockville, Md. and has been assigned the following accession number:

| *E. coli* Strains | Plasmid | Accession Number |
|---|---|---|
| *E. coli* HB101 | p97b | 53,403 |

The following recombinant vaccinia virus has been deposited with the ATCC, Rockville, Md., and has been assigned the following accession number:

| Virus | Accession Number |
|---|---|
| Vp97a-NY | VR 2159 |

The following cell lines carrying the listed plasmids have been deposited with the ATCC, Rockville, Md., and have been assigned the following accession numbers:

| Cell Line | Plasmid | Accession Number |
|---|---|---|
| TKMp97-12 (Mouse cell) | PMTp97b | CRL 8985 |
| B16SVp97a.14 (mouse melanoma cell) | pSVp97a | CRL 9304 |

The present invention is not to be limited in scope by the microorganisms and cells deposited since the deposited embodiment is intended as single illustration of one aspect of the invention and any microorganisms or cells which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair sizes given for nucleotides are approximate and are used for purpose of description.

What is claimed is:

1. A recombinant virus, the genome of which comprises a nucleotide sequence encoding a melanoma-associated p97 antigen or an antigenic portion thereof, which is under the control of a second nucleotide sequence that regulates gene expression so that a melanoma associated p97 antigen, or an antigenic portion thereof, is expressed in a host infected with the virus.

2. A recombinant virus the genome of which comprises a nucleotide sequence encoding a melanoma-associated p97 antigen, or an antigenic portion thereof, which comprises the nucleotide sequence substantially as depicted in FIG. 3 or any portion thereof encoding an antigenic peptide or protein, and which is under the control of a second nucleotide sequence that regulates gene expression so that a melanoma-associated p97 antigen, or an antigenic portion thereof, is expressed in a host infected with the virus.

3. The virus according to claim 1 or 2 comprising an enveloped virus.

4. The virus according to claim 3 comprising a vaccinia virus.

5. The virus according to claim 1 or 2 comprising a naked virus.

6. The virus according to claim 5 comprising an adenovirus.

7. The virus according to claim 1 or 2 comprising a baculovirus.

8. The virus according to claim 7 comprising a nuclear polyhedrosis virus.

9. The virus according to claim 1 or 2 comprising a bacteriophage.

10. The virus according to claim 9 comprising a lambda phage.

11. A live virus immunogenic formulation comprising the recombinant virus of claim 1 or 2 in which the virus is infectious without causing disease in a host to be immunized.

12. The live virus immunogenic formulation of claim 11 in which the recombinant virus comprises an enveloped virus.

13. The live virus immunogenic formulation of claim 12 in which the enveloped virus comprises a vaccinia virus.

14. The live virus immunogenic formulation of claim 11 in which the recombinant virus comprise a naked virus.

15. The live virus immunogenic formulation of claim 14 in which the naked virus comprises an adenovirus.

16. An inactivated virus immunogenic formulation comprising an effective dose of the recombinant virus of claim 1 or 2 in a non-infections state mixed with a pharmaceutical carrier.

17. An inactivated virus immunogenic formulation comprising an effective dose of the recombinant virus of claim 3 in a non-infections state mixed with a pharmaceutical carrier.

18. An inactivated virus immunogenic formulation comprising an effective dose of the recombinant virus of claim 4 in a non-infections state mixed with a pharmaceutical carrier.

19. An inactivated virus immunogenic formulation comprising an effective dose of the recombinant virus of claim 5 in a non-infections state mixed with a pharmaceutical carrier.

20. An inactivated virus immunogenic formulation comprising an effective dose of the recombinant virus of claim 6 in a non-infections state mixed with a pharmaceutical carrier.

21. An inactivated virus immunogenic formulation comprising an effective dose of the recombinant virus of claim 7 in a non-infectious state mixed with a pharmaceutical carrier.

22. An inactivated virus immunogenic formulation comprising an effective dose of the recombinant virus of claim 8 in a non-infections state mixed with a pharmaceutical carrier.

23. An inactivated virus immunogenic formulation comprising an effective dose of the recombinant virus of claim 9 in a non-infections state mixed with a pharmaceutical carrier.

24. A recombinant DNA vector comprising p97b.

25. A unicellular organism containing the recombinant DNA vector of claim 24.

26. A bacterium containing the recombinant DNA vector of claim 24.

27. A bacterium of claim 26 comprising *Escherichia coli* as deposited with the ATCC and assigned accession number 53403, or a mutant, recombinant or genetically engineered derivative thereof.

28. A recombinant DNA vector comprising. pMTp97b.

29. A cell line containing the recombinant DNA vector of claim 28.

30. The cell line of claim 28 comprising TKMp97-12 as deposited with the ATCC and assigned accession number CRL 8985 or a mutant, recombinant or genetically engineered derivative thereof.

31. A recombinant DNA vector comprising pSVp97a.

32. A cell line containing the recombinant DNA vector of claim 31.

33. The cell line of claim 22 comprising B16SVp97a.14 as deposited with the ATCC and assigned accession number CRL 9304 or a mutant, recombinant or genetically engineered derivative thereof.

34. The virus according to claim 4 comprising virus Vp97a-NY as deposited with the ATCC and assigned accession number VR 2159, or a mutant, recombinant or genetically engineered derivative thereof.

* * * * *